United States Patent
Hümmerich et al.

(10) Patent No.: US 9,481,719 B2
(45) Date of Patent: Nov. 1, 2016

(54) RECOMBINANT PRODUCTION OF PEPTIDES

(75) Inventors: Daniel Hümmerich, Frankenthal (DE); Burghard Liebmann, Bensheim (DE); Marcus Fehr, Speyer (DE); Carsten Schwalb, Mannheim (DE); Heike Brüser, Speyer (DE)

(73) Assignee: BASF SE, Ludwigshafen (DE)

( * ) Notice: Subject to any disclaimer, the term of this patent is extended or adjusted under 35 U.S.C. 154(b) by 1079 days.

(21) Appl. No.: 13/375,559

(22) PCT Filed: Jun. 2, 2010

(86) PCT No.: PCT/EP2010/057726
§ 371 (c)(1),
(2), (4) Date: Dec. 1, 2011

(87) PCT Pub. No.: WO2010/139736
PCT Pub. Date: Dec. 9, 2010

(65) Prior Publication Data
US 2012/0088268 A1    Apr. 12, 2012

(30) Foreign Application Priority Data
Jun. 3, 2009    (EP) ..................... 09161837

(51) Int. Cl.
| C07K 14/47 | (2006.01) |
| C07K 19/00 | (2006.01) |
| C12N 15/62 | (2006.01) |
| C12P 21/06 | (2006.01) |

(52) U.S. Cl.
CPC ........... *C07K 14/4723* (2013.01); *C12N 15/62* (2013.01); *C12P 21/06* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| 6,800,727 B2 | 10/2004 | Hahm et al. |
| 8,455,490 B2 | 6/2013 | DeGrado et al. |
| 2003/0096745 A1 | 5/2003 | Hahm et al. |
| 2003/0219854 A1 | 11/2003 | Guarna et al. |
| 2008/0109923 A1* | 5/2008 | Roth et al. .................... 800/298 |
| 2010/0216189 A1 | 8/2010 | Liebmann et al. |
| 2010/0278883 A1 | 11/2010 | Liebmann et al. |

FOREIGN PATENT DOCUMENTS

| KR | 1998-0702853 A | 8/1998 |
| KR | 2006-0015479 A | 2/2006 |
| RU | 2 336 278 C2 | 10/2008 |
| WO | WO-96/28468 A2 | 9/1996 |
| WO | WO-98/54336 A1 | 12/1998 |
| WO | WO-00/31279 A2 | 6/2000 |
| WO | WO-03/044049 A1 | 5/2003 |
| WO | WO-03089455 A2 | 10/2003 |
| WO | WO-2006/008163 A2 | 1/2006 |
| WO | WO-2007/082936 A1 | 7/2007 |
| WO | WO-2008085543 A2 | 7/2008 |
| WO | WO-2008/155304 A1 | 12/2008 |
| WO | WO-2009/080306 A1 | 7/2009 |

OTHER PUBLICATIONS

Jenkins et al., Characterizing the secondary protein structure of black widow dragline silk using sold-state NMR and X-ray diffraction, Biomacromolecules, 2013, 14, 3472-83.*
Gertler et al., Purification and characterization of porcine elastase II and investigation of its elastolytic specificity, Biochemistry, 1977, 16, 2709-16.*
McPherson et al., Chapter 4: Recombinant Production of self-assembling peptides, Adv. Chem. Eng., 2009, 35, 79-117.*
Winkler et al., Designing recombinant spider silk proteins to control assembly, Int. J. Biol. Macromol., 1999, 24, 265-270.*
Crimmins et al., Current Protocols in Protein Science, 2005, 11.4.1-11.4.11.*
Hancock, R.E.W. et al., "Cationic Peptides: A New Source of Antibiotics." *TIBTECH*, 16, Feb. 1998, 82-88.
Hancock, R.E.W. et al., "Antimicrobial and host-defense peptides as new anti-infective therapeutic strategies." *Nature Biotechnology*, 24, 2006, p. 1551-1557.
Huemmerich, D. et al., "Primary Structure Elements of Spider Dragline Silks and Their Contribution to Protein Solubility." *Biochemistry*, 43, 2004, p. 13604-13612.
Kim, H.K. et al., "Expression of the cationic antimicrobial peptide lactoferricin fused with the anionic peptide in *Escherichia coli*." *Applied Microbiol. Biotechnol.* 72, 2006, p. 330-338.
Lee, D.G. et al., "Structure and fungicidal activity of a synthetic antimicrobial peptide, P18, and its truncated peptides." *Biotechnology Letters*, 26, 2004, p. 337-341.
Lee, J.H. et al., "Acidic Peptide-Mediated Expression of the Antimicrobial Peptide Buforin II as Tandem Repeats in *Escherichia coli*." *Protein Expression and Purification*, 12, 1998, p. 53-60.
Li, Y. "Carrier proteins for fusion expression of antimicrobial peptides in *Escherichia coli*." *Biotechnol. Appl. Biochem.* 54, 2009, p. 1-9.
Metlitskaia, L. et al., "Recombinant antimicrobial peptides efficiently produced using novel cloning and purification processes." *Biotechnol. Appl. Biochem.*, 39, 2004, p. 339-345.
Shin, S.Y. et al., "Cicropin A—Magainin 2 hybrid peptides having potent antimicrobial activity with low hemolytic effect." *Biochem. Mol. Biol. Int.*, 44, 1998, p. 1119-1126.
Shin, S.Y. et al., "Structure-antibacterial, antitumor and hemolytic activity relationships of cecropin A-magainin 2 and cecropin A-melittin hybrid peptides." *J. Peptide Res.*; 53, 1999, p. 82-90.
Vassilevski, A.A. et al., "Antimicrogial peptide precursor structures suggest effective production strategies." *Recent Patents on Inflammation & Allergy Drug Discovery*, 2, p. 58-63.

(Continued)

*Primary Examiner* — Robert Mondesi
*Assistant Examiner* — Todd M Epstein
(74) *Attorney, Agent, or Firm* — Drinker Biddle & Reath LLP

(57) ABSTRACT

The present invention relates to repetitive self-assembling precursor proteins, nucleic acid sequences and expression constructs encoding the same, and to methods for recombinant production of peptides using such precursor proteins.

17 Claims, 11 Drawing Sheets

(56) References Cited

OTHER PUBLICATIONS

Wade, D. et al., "Antibacterial peptides designed as analogs or hybrids of cecropins and melittin." *Int. J. Peptide Protein Res.*, 40, 1992, p. 429-436.

Wang, Y.Q. et al., High-level expression of acidic partner-mediated antimicrobial peptide from tandem genes in *Escherichia coli*. *Applied Biochemistry and Biotechnology*, 141, 2007, p. 203-214.

Giri, K., et al., "pH-Dependent Self-Assembly of Polyalanine Peptides", Biophysical Journal, 2007, vol. 92, No. 1, pp. 293-302.

* cited by examiner

A)   A1 – A2 – A3 – A4 – A5 – A6 – A7

B)

US 9,481,719 B2

RECOMBINANT PRODUCTION OF PEPTIDES

RELATED APPLICATIONS

This application is a national stage application (under 35 U.S.C. §371) of PCT/EP2010/057726, filed Jun. 2, 2010 which claims benefit of European Application No. 09161837.1, filed Jun. 3, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00197_US. The size of the text file is 37 KB, and the text file was created on Nov. 30, 2011.

The present invention relates to repetitive self-assembling precursor proteins, nucleic acid sequences and expression constructs coding therefor, and to methods of recombinantly producing peptides by using such precursor proteins.

BACKGROUND OF THE INVENTION

There are different known methods of producing peptides by biotechnological means. Since the stability of short polypeptide chains in microbial host cells is usually low, and since the free peptides may have a possible toxic effect on the host organism (for example antimicrobial peptides), most methods involve producing larger precursor proteins from which the peptide is excised after the precursor protein has been purified.

One possibility of obtaining a stable precursor protein comprises expressing a peptide together with a stable protein by way of a fusion protein. The properties of said fusion protein, which greatly influence subsequent work-up steps, are determined by the fusion partner largely independently of the peptide sequence, and are therefore readily controllable and suitable for producing peptides with different sequences.

WO 2008/085543 describes a special method of producing proteins and peptides with the aid of a fusion protein. This fusion protein comprises aside from the desired peptide sequence a fusion partner which ensures that the fusion protein exhibits an inverse phase transition behavior. This behavior firstly involves the fusion protein to be purified from the cellular context in a simple and inexpensive manner. Secondly, the fusion partner may likewise be removed in a simple and inexpensive manner, after the peptide has been removed by proteolytical cleavage. While a fusion protein may frequently be obtained with good yields, the peptide portion of the precursor protein is usually small, and the efficiency of the process is therefore suboptimal.

Another approach involves repetitive precursor proteins which comprise multiple copies of the desired peptide being recombinantly produced. WO 03/089455 describes the production of multimeric precursor proteins from which the desired peptide sequences which have antimicrobial properties are excised by acidic cleavage.

There are a number of further published approaches (examples: Metlitskaya et al. Biotechnol Appl. Biochem 39; 339-345 (2004); Wang & Cai Appl. Biochem and Biotechnol. 141; 203-213 (2007)), which were used for demonstrating that peptide sequences or families of peptide sequences may be produced by a particular method with the aid of repetitive precursor proteins. To some extent the use of special auxiliary sequences which are located between the repeats of the desired peptide sequences has been described. More specifically, anionic auxiliary sequences have been proposed which apparently reduce the harmful action of cationic antimicrobial peptide sequences within a repetitive precursor protein on the host cell (cf. for example WO 00/31279 and US 2003/0219854). While the precursor protein in this repetitive approach has a higher proportion of the desired peptide sequence than is the case with fusion proteins, the properties of the repetitive precursor proteins are greatly influenced by the sequence of the desired cationic peptide.

The inventors have no knowledge of any previous method involving the possibility of producing any peptide sequences with the aid of repetitive precursor proteins according to a simple, low-cost protocol which can be carried out in an efficient manner.

Various antimicrobial peptides have been described in the literature and are summarized in Reviews (Hancock, R. E. W. and Lehrer, R. 1998 in Trends in Biotechnology, 16: 82-88; Hancock, R. E. W. and Sahl, H. G. 2006 in Nature Biotechnology, 24: 1551-1557).

Fusion peptides, in which two active peptides are combined, are likewise described in the literature. Wade et al. report the antibacterial action of various fusions of *Hyalophora cecropia* cecropin A and the poison melittin (Wade, D. et al., 1992, International Journal of Peptide and Protein Research, 40: 429-436). Shin et al. describe the antibacterial action of a fusion peptide of *Hyalophora cecropia* cecropin A and *Xenopus laevis* magainin 2, consisting of 20 amino acids. Cecropin A consists of 37 amino acids and exhibits activity against Gram-negative bacteria that lower activity against Gram-positive bacteria. magainin 2 consists of 23 amino acids and is active against bacteria but also tumor cell lines. Compared with the fusion of cecropin A and melittin, this fusion exhibits a distinctly lower hemolytic activity with a comparable antibacterial action (Shin, S. Y. Kang, J. H., Lee, M. K., Kim, S. Y., Kim, Y., Hahm, K. S., 1998, Biochemistry and Molecular Biology International, 44: 1119-1126). US 2003/0096745 A1 and U.S. Pat. No. 6,800,727 B2 claim these fusion peptides, consisting of 20 amino acids, and variants of said fusion which, due to the substitution of amino acids, in particular of positively charged amino acids and hydrophobic amino acids, are more positively charged and more hydrophobic.

Shin et al., 1999, describe further developments of this cecropin A-magainin 2 fusion peptide. They demonstrated that the peptide having SEQ ID NO:6 had a lower hemolytic activity compared to the starting fusion but that the antibacterial activity with respect to *Escherichia coli* and *Bacillus subtilis* was not adversely affected (Shin at al. 1999 Journal of Peptide Research, 53: 82-90).

BRIEF DESCRIPTION OF THE INVENTION

It was therefore an object of the present invention to provide a widely applicable method of producing peptides with the aid of repetitive precursor proteins.

This object was achieved by a novel approach of producing peptides by biotechnological means, with repetitive precursor proteins being produced which comprise a high proportion of the desired peptide sequence and which comprise the auxiliary sequences which dominate the properties of the precursor protein in a predictable manner. Said method may be used for producing different peptide sequences without having to reestablish fundamentally the conditions for expressing the precursor molecule or the subsequent work-up procedure for each of the different peptide sequences. It is moreover possible to produce peptides for which previously used methods are not efficient.

DESCRIPTION OF THE FIGURES

In the accompanying figures.

PREFERRED EMBODIMENTS

Figure 1:
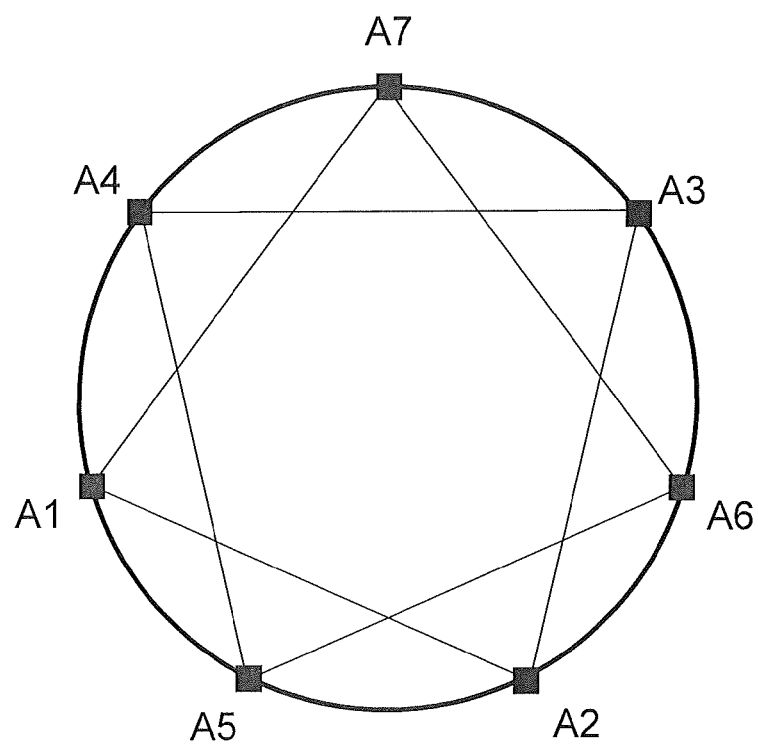
FIG. 1 depicts a helical wheel representation of amino acid sequences by way of projecting an alpha-helix structure. The amino acid sequence comprised in the repetitive precursor protein, A1-A7 (A), is depicted on a circle (B). This arrangement visualizes the position of the amino acids in an alpha-helix.

The invention particularly relates to the following embodiments:

1. A synthetic, in particular recombinantly prepared precursor protein comprising an enzymatically and/or chemically cleavable repetitive sequence of repeats of desired peptide (Pep) elements and auxiliary peptide (Aux) elements of the general formula $(Pep-Aux)_x$ or $(Aux-Pep)_x$ where x>1, wherein
the Aux elements are identical or different and comprise amino acid sequence elements which impart to said precursor protein self-assembling properties; and the Pep elements are identical or different and comprise the amino acid sequence of identical or different peptide molecules.

2. A precursor protein according to embodiment 1, wherein the elements Pep and Aux are peptidically linked to one another directly or via a cleavable peptide sequence, and the peptidic linkage is specifically cleavable chemically or enzymatically, i.e. exclusively or essentially cleavable on a defined amino acid or sequence of amino acids of a sequence.

3. A precursor protein according to either of the preceding embodiments, which has self-assembling properties so as to form spontaneously, i.e. by itself, or inducibly stable, non-covalent associates which cannot be dissolved at room temperature under standard conditions, such as in particular by 0.2 M NaOH inside one hour or by 2 M urea or 1 M guanidinium hydrochloride in each case inside 10 min. A stable associate according to the invention results from at least one of these three criteria mentioned being satisfied.

4. A precursor protein according to any of the preceding embodiments, wherein at least one Aux element comprises a self-assembling peptide (SA) element, wherein said SA element comprises at least one sequence motif of at least 8, such as, for example, 8-10, 8-12, 8-14, 8-16, 8-18 or 8-20, continuous amino acids, which comprises at least 50%, for example 50-100%, 60-90% or 70-80%, alanine residues, at least 50%, for example 50-100%, 60-90% or 70-80%, valine residues, or at least 50%, for example 50-100%, 60-90% or 70-80%, glutamine residues, or at least 80% of which consists of at least one of these residues; the SA element may comprise, for example, in particular at least one of the following sequence motifs:

$A_n$ (motif 1)
$(GA)_m$ (motif 2)
$V_n$ (motif 3)
$(VA)_m$ (motif 4)
$(VVAA)_o$ (motif 5)

wherein A is alanine, G is glycine, V is valine, n is an integer from 2 to 12, m is an integer from 2 to 10, and o is an integer from 1 to 6, where more especially n=5-10, m=4-8, and o=2-4, for example n=7-9, m=6-7 and o=2-3.

The above SA sequences may be elongated C- and/or N-terminally by in each case a further 1 to 3 random amino acid residues. Examples of suitable N-terminal elongations are the sequence motifs "G-", "GS-", "GAG-", "GPG-", "GPS-", "GAS-", "GQQ-" and "GSS-"; examples of suitable C-terminal elongations comprise the sequence motif "-SGP", "-GGA", "-GPG", "-SGA", "-GGQ", "-GGY" and "-GGL".

5. A precursor protein according to embodiment 4, wherein the SA element comprises an amino acid sequence selected from among the amino acid sequences SEQ ID NO: 1 to SEQ ID NO:5, or SED ID No:73.

6. A precursor protein according to any of the preceding embodiments, wherein at least one Aux peptide additionally comprises a protective peptide (SU) element.

7. A precursor protein according to embodiment 6, wherein the SU element has an "increased proportion" of charged, i.e. (for example at pH=7) an overall charge different from 0, for example from +20 to −20 or +10 to −10 or +5 to −5, amino acid residues, in particular negatively charged, amino acid residues, for example at pH=7, an overall charge different from 0, for example from −1 to −20, in particular −4 to −10.
8. A precursor protein according to embodiment 7, wherein the SU element in the precursor protein is capable of forming an amphiphilic helical structure.
9. A precursor protein according to embodiment 8, wherein the SU element is an amphiphilic peptide comprising a sequence segment of at least seven peptidically linked amino acids capable of forming an amphiphilic alpha-helix, wherein the amino acid residues of said helix in its vertical projection are separated into a hydrophobic half and a hydrophilic half of the helix, the hydrophobic half of the helix having at least 3 adjacent, for example 3 or 4 in the vertical projection, identical or different hydrophobic amino acid residues, and the hydrophilic half of the helix having at least 3 adjacent, for example 3 or 4 in the vertical projection, identical or different hydrophilic amino acid residues.
10. A precursor protein according to embodiment 7, 8 or 9, wherein the proportion of charged amino acid residues of the SU element is chosen such that the overall net charge of the precursor protein at pH=7 is greater than −10 and less than +10, for example greater than −8 and less than +8; greater than −5 and/or less than +5, greater than −2 and less than +2.
11. The precursor protein according to any of the embodiments 7 to 10, wherein the SU element comprises an amino acid sequence selected from among the amino acid sequences SEQ ID NO: 16 to SEQ ID NO:19 and SEQ ID NO: 68.
12. A precursor protein according to any of the preceding embodiments, wherein the Pep element comprises an antimicrobial peptide sequence having a cationic positive overall charge.
13. A precursor protein according to embodiment 12, wherein the Pep element comprises an amino acid sequence selected from among the cationic amino acid sequences SEQ ID NO: 6 to SEQ ID NO:15, SEQ ID NO: 23, SEQ ID NO: 26 and SEQ ID NO: 69 to SEQ ID NO: 72 or any of the C-terminally and/or N-terminally modified forms thereof indicated below.
14. A precursor protein according to any of the embodiments 1 to 5, wherein the Pep peptide comprises an amino acid sequence selected from among the amino acid sequences SEQ ID NO: 20 or SEQ ID NO: 29 to 67 or any of the C-terminally and/or N-terminally modified forms thereof indicated below.
15. A precursor protein according to any of the preceding embodiments, wherein the Aux elements independently of one another have any of the following meanings:
SA,
SA-SU,
SU-SA,
SA-SU-SA,
SU-SA-SU,
wherein the elements SA and SU are peptidically linked to one another, and the Aux elements are peptidically linked terminally to at least one Pep element peptidically, i.e. directly or via a cleavable peptide sequence, wherein at least the peptidic linkage to the Pep elements is specifically cleavable chemically or enzymatically.
16. A nucleic acid sequence coding for at least one precursor protein according to any of the preceding embodiments.
17. A nucleic acid sequence according to embodiment 16, comprising at least one coding sequence of SEQ ID NO: 21, 24; 27; 74 and 76.
18. An expression cassette comprising at least one nucleic acid sequence according to embodiment 16 or 17, operatively linked to at least one regulatory nucleic acid sequence.
19. A recombinant vector for transforming a eukaryotic or prokaryotic host, comprising a nucleic acid sequence according to either of embodiments 16 and 17, or an expression cassette according to embodiment 18.
20. A method of producing a desired peptide (Pep), which comprises
    a) producing a precursor protein according to any of embodiments 1 to 15,
    b) removing the Pep peptides from the precursor protein; and
    c) optionally enzymatically or chemically modifying, such as, for example, amidating, esterifying, oxidizing, alkylating, the peptide or linking it (for example by native chemical ligation or by a Michael addition) to another molecule; wherein, for example, the peptide is modified with a molecule that increases the hydrophobicity of said peptide, for example modified with a molecule comprising an alkyl radical; wherein it is possible for said modification to be carried out before or after optional purification of the peptide, as will also be illustrated further by the accompanying examples. Examples of suitable alkyl radicals are $C_2$-$C_{16}$-alkyl radicals such as ethyl, isopropyl or n-propyl, n-butyl, isobutyl, sec- or tert-butyl, n-pentyl or isopentyl; also n-hexyl, n-heptyl, n-octyl, n-nonyl, n-decyl, n-undecyl, n-dodecyl, n-tridecyl, n-tetradecyl, n-pentadecyl and n-hexadecyl, and the singly or multiply branched analogs thereof, and unsubstituted or substituted modifications thereof which may have one or more, for example 1, 2 or 3, halogen (such as F, Cl, Br, for example), hydroxyl, mercapto, amino, $C_1$-$C_4$-alkylamino substituents, or may be interrupted by one or more, for example 1, 2 or 3, heteroatoms such as O or N in the alkyl chain. More specifically, $C_1$-$C_4$-alkyl is methyl, ethyl, isopropyl or n-propyl, n-butyl, isobutyl, sec- or tert-butyl.
21. A method according to embodiment 20, wherein the precursor protein is produced in a recombinant microorganism carrying at least one vector according to embodiment 19.
22. A method according to embodiment 21, wherein the precursor protein is produced in a recombinant E. coli strain.
23. A method according to any of embodiments 20 to 22, wherein the expressed precursor protein, optionally after having been converted into a stably associated form, is purified and cleaved chemically or enzymatically to release the desired peptide (Pep).
24. A precursor protein comprising a cleavable sequence of desired peptide (Pep) elements and auxiliary peptide (Aux') elements of the general formula $$(Pep\text{-}Aux')_x$$

or $$(Aux'\text{-}Pep)_x$$

where x>1, wherein
the Aux' elements are identical or different and comprise an amphiphilic alpha-helix-forming peptide, said amphiphilic peptide comprising a sequence segment of at least seven peptidically linked amino acids capable of forming an amphiphilic alpha-helix, wherein the amino acid residues of said helix in its vertical projection are separated into a hydrophobic half and a hydrophilic half of the helix, the hydrophobic half of the helix having at least 3 adjacent, for example 3 or 4 in the vertical projection, identical or different hydrophobic amino acid residues, and the hydrophilic half of the helix having at least 3 adjacent, for example 3 or 4 in the vertical projection, identical or different hydrophilic amino acid residues; and the Pep elements are identical or different and comprise the amino acid sequence of identical or different peptide molecules.

25. A precursor protein according to embodiment 24, wherein the Aux' elements comprise at least one self-assembling peptide (SA) element as defined in any of embodiments 4 and 5.

26. The precursor protein according to embodiment 24 or 25, wherein the desired peptide (Pep) is a cationic antimicrobial peptide, and the Aux' element is an anionic peptide forming an amphiphilic alpha-helix.

27. The use of an amphiphilic peptide as protective peptide for recombinantly producing an antimicrobial desired peptide different therefrom; wherein said amphiphilic peptide comprises a sequence section of at least seven peptidically linked amino acids capable of forming an amphiphilic alpha-helix, wherein the amino acid residues of said helix in its vertical projection are separated into a hydrophobic half and a hydrophilic half of the helix, the hydrophobic half of the helix having at least 3 adjacent (in the vertical projection) identical or different hydrophobic amino acid residues, and the hydrophilic half of the helix having at least 3 adjacent (in the vertical projection) identical or different hydrophilic amino acid residues.

28. The use according to embodiment 27, wherein the desired peptide (Pep) is a cationic antimicrobial peptide, and the Aux' element is an anionic peptide forming an amphiphilic alpha-helix.

29. A method according to any of embodiments 20 to 22, wherein a precursor protein according to embodiment 12 or 13 such as, for example, a precursor protein comprising P18 peptide building blocks according to SEQ ID NO:23 or SEQ ID NO:6 is produced.

30. A method according to embodiment 29, which includes the following work-up steps:
   Washing the precursor protein associates with a solvent which dissolves contaminating proteins but not, or essentially not, said associates, such as 0.1 M to 1.0 M NaOH, for example.
   Cleaving the precursor proteins, for example with an acid, if the desired peptide, for example P18, is incorporated in the precursor protein via acid-cleavable groups.

31. A method according to embodiment 30, which includes at least one of the following additional work-up steps:
   Treating the precursor protein associates with an auxiliary precipitant such as phosphoric acid for example, after cell disruption
   Purifying the peptide cleavage reaction mixture using a chromatographic method;
   Washing the purified and dried peptide with an acidic solvent or solvent mixture.

32. A method according to any of embodiments 20 to 23 and 29 to 31 for producing the peptide of SEQ ID NO:23, which method includes the following work-up steps:
   Treating the precursor protein associates after cell disruption by adding 85% strength phosphoric acid, until pH=3.
   Washing the precursor protein associates with a sodium hydroxide solution, for example 0.4 M NaOH
   Cleaving the precursor protein with phosphoric acid or formic acid, for example 2% phosphoric acid
   Optionally washing the dried peptide with hexanoic acid or a mixture of 99 parts of hexane and one part of acetic acid.

33. A method according to any of the embodiments 20 to 23 and 29 to 31 for producing the peptide of SEQ ID NO:6, which method includes the following work-up steps:
   Hydrolysing or cleaving the pellets, for example by means of 5% strength $H_3PO_4$;
   Centrifugation;
   Adjusting the pH of the supernatant to about 4.0, for example with 25% NaOH
   Purifying the supernatant using cation exchange chromatography
   Precipitating the desired peptide, for example by adding NaOH to the eluate
   Centrifugation;
   Resuspending the pellet in water
   Dissolving the peptide, for example by adding acetic acid
   Lyophilization.

34. The invention furthermore relates to the P18 peptide (SEQ ID NO:23) and the peptide SEQ ID NO: 6 and production thereof according to the invention, and to the use thereof in cosmetic or pharmaceutical means for treating or preventing scales, in particular dandruff; or for inhibiting the growth and/or activity of lipophilic fungi, in particular *Malassezia* ssp., particularly *Malassezia furfur*. This is also described, for example, in the older international application PCT/EP2008/010912, filing date Dec. 19, 2008, the disclosure of which is hereby explicitly referred to.

DETAILED DESCRIPTION OF INDIVIDUAL ASPECTS OF THE INVENTION

1. Peptides

Peptides (Pep) according to the present invention, which may also be referred to as "desired peptides" or "target peptides", are amino acid chains in which from 2 to 100, for example 5 to 70 and in particular 7 to 50, for example 10 to 40, 12 to 35 or 15 to 25, amino acids are linked via peptide bonds. Peptides may be composed of any α-amino acids, in particular the proteinogenic amino acids.

The peptides may have particular desired biological or chemical and in particular also pharmacologically usable properties. Examples of such properties are: antimicrobial activity, specific binding to certain surfaces, nucleating properties in crystallization processes and particle formation, control of crystal structures, binding of metals or metal ions, surfactant properties, emulsifying properties, foam-stabilizing properties, influencing cellular adsorption.

Said peptides may have one or more of these properties.

In one embodiment, the invention relates to a method of producing antimicrobial peptides. Such "antimicrobial peptides" are distinguished by the growth and/or propagation of at least one type of gram-positive or gram-negative bacteria and/or at least one type of yeast and/or at least one type of filamentous fungi and/or at least one type of algae being inhibited and/or the cells of the respective organism being destroyed in the presence of concentrations of the antimicrobial peptide of ≤100 μM.

In one embodiment, the invention relates to providing cationic antimicrobial peptides. Cationic antimicrobial peptides are distinguished by having an antimicrobial action as defined above and a net charge of greater than 0 at pH 7.

Cationic peptides of this kind comprise, for example, the following sequence:

$$X_1\ X_2K\ X_3\ X_4\ X_5KIP\ X_{10}\ KFX_6X_7\ X_8\ AX_9KF \quad \text{(SEQ ID NO: 7)}$$

in which
$X_{10}$ is a peptide bond or any one or two basic or hydrophobic amino acid residues or one or two proline residues, and
$X_1$ to $X_9$ are any basic or hydrophobic amino acid residues other than proline;
and/or mutants or derivatives thereof;
wherein the repetitive sequence motifs present in the precursor protein may be identical or different.

In a further special embodiment, the invention relates to producing peptides comprising the following sequence:

$$X_1\ X_2K\ X_3\ X_4\ X_5KIP\ X_{11}\ X_{12}\ KFX_6X_7\ X_8\ AX_9KF \quad \text{(SEQ ID NO: 8)}$$

in which
$X_1$ is lysine, arginine or phenylalanine,
$X_2$ is lysine or tryptophan,
$X_3$ is leucine or lysine,
$X_4$ is phenylalanine or leucine,
$X_5$ is leucine or lysine,
$X_6$ is leucine or lysine,
$X_7$ is histidine or lysine,
$X_8$ is alanine, leucine, valine or serine,
$X_9$ is leucine or lysine,
$X_{11}$ is proline or a chemical bond, and
$X_{12}$ is proline or a chemical bond,
and/or mutants and derivatives thereof;
wherein the repetitive sequence motifs present in the precursor protein are identical or different.

Non-limiting examples of the above sequences or repetitive sequence motifs are SEQ ID NO:6, SEQ ID NO:9-SEQ ID NO:15, SEQ ID NO:23, SEQ ID NO:69, SEQ ID NO:71, and/or a mutant or derivatives thereof.

Other suitable peptides are described, for example, in the international application of the present applicant, PCT/EP2008/010912, filing date Dec. 19, 2008, which is hereby explicitly referred to.

2. Repetitive Precursor Proteins

Repetitive precursor proteins according to the present invention are distinguished by at least 60%, in particular at least 80%, of their amino acid sequence, for example 60-99%, 70-95%, 75-85%, in each case based on total sequence length, consist of peptidic repeats (as defined hereinbelow). The remaining portion may comprise, for example, non-repetitive peptides such as, for example, signal peptides, tags and the like.

3. Repeats

Peptidic repeats comprise at least one peptide produced advantageously according to the present invention, and, in principle, are constructed as follows (Pep-Aux)$_x$ or (Aux-Pep)$_x$ where x>1, and with Pep being the peptide denoted above and Aux being as defined herein.

A repeat (Pep-Aux, or Aux-Pep) according to the present invention is an amino acid sequence of 10-200, for example 20-130 and/or 30-80, amino acids in length, which is present in a precursor protein a plurality of times, either as identical sequences or as variations of a particular sequence having at least 70%, for example at least 80% and in particular at least about 90%, identity, for example 91, 92, 93, 94, 95, 96, 97, 98 or 99% identity. Repetitive precursor proteins according to the present invention may thus comprise, for example, identical copies or variations of a single amino acid sequence or of multiple different amino acid sequences, for example of the Pep and/or the Aux building blocks.

Moreover, any number of the above repeats, for example 1-100, 1-50, or 2-32 and in particular 4-16, may be joined together in a repetitive precursor protein.

The proportion of the peptide according to the invention in the repeat, based on the molar mass, is 20%-80%, for example 30%-70%. The remaining part of the repeat is made up by the Aux sequences, in particular the SA and SU sequences defined above, and optionally specific cleavage sequences for selectively removing the Pep building block.

4. Auxiliary Sequences

Auxiliary sequences in the broadest sense are amino acid sequences in a precursor protein according to the invention which influence the properties of said precursor protein so as to improve expression, stability and/or work-up of said precursor protein. Auxiliary sequences in a repetitive precursor protein may be part of a repeat (the Aux building blocks indicated above) or may be attached to the amino terminus or carboxy terminus of the precursor protein, such as, for example, 6×His tag (HHHHHH), T7 tag (MASMTG-GQQMG), S tag (KETAAAKFERQHMDS), c-Myc tag (EQKLISEEDL), Strep tag (WSHPQFEK) or HA tag (YPY-DVPDYA), glutathione S-transferase, maltose binding protein, cellulose binding protein. These and other auxiliary sequences are described in Terpe; Appl Microbiol Biotechnol; 60(5): 523-33 (2003). Furthermore, the auxiliary sequences CanA (Mai, In Vitro Untersuchungen zum extrazellulären Netzwerk von *Pyrodictium abyssi* TAG11" [In Vitro Studies of the Extracellular Network of *Pyrodictium abyssi* TAG11], PhD Theses, Regensburg University (1998)) and yaaD (Wohlleben Eur Biophys J, (2009) online publication) are useful for being attached to the amino terminus or carboxy terminus of the precursor protein.

In one embodiment, the precursor protein comprises auxiliary sequences which influence the solubility of said precursor protein.

In a preferred embodiment, the auxiliary sequences impart "self-assembling" properties to the precursor protein. Said self-assembling properties of the precursor protein are distinguished by said precursor protein forming stable associates "spontaneously", i.e. by itself, without additionally required measures, already during expression or by the formation of such stable associates of soluble precursor proteins possibly being started in an "inducible" manner, i.e. by a trigger. Precursor proteins having self-assembling properties are advantageous over other precursor proteins in that they may be purified in a simple and efficient manner. Associates of this kind usually comprise exclusively or essentially the formation of noncovalent bonds such as, for example, hydrogen bonds, ionic and/or hydrophobic interactions.

Self-assembling sequences may be, for example, at least 8 contiguous amino acids in length. Suitable sequences may be located, for example, in proteins known per se in which assembling into associates of higher molecular weight has been detected previously. Examples of such associates are amyloid fibrils, actin or myosin filaments, protein fibers such as elastin fibers, collagen fibers, musselbyssus threads, keratin fibers, or silk threads. These and other proteins comprising self-assembling sequences are described in Scheibel, Current Opinion in Biotechnology 16; 1-7 (2005), which is hereby explicitly referred to.

Solutions of cosmotropic salts may be employed as "triggers". Cosmotropic salts which may be mentioned here by way of example are those comprising at least one type of ion that has more pronounced cosmotropic properties than sodium or chloride ions, according to the "Hofmeister" series. Examples of such salts are potassium phosphate and ammonium sulfate. Examples of such salt solutions are 0.5 M potassium phosphate and 0.8 M ammonium sulfate.

Stable associates according to the invention of precursor proteins are distinguished by maintaining their associated form over a certain period during the treatment with solutions typically capable of solubilizing a multiplicity of aggregated proteins, and in this way being able to be separated from protein contaminations. Examples of such solutions are solutions of bases, acids, urea, salts and detergents. More specifically, the stable associates according to the invention are insoluble over a certain period in solutions of alkali metal hydroxides, urea, guanidinium salts or charged detergents such as, for example, alkyltrimethylammonium salts or alkyl sulfates.

More specifically, the stable associates are insoluble for a certain period in solutions of ≥0.2 M sodium hydroxide, ≥2 M urea, ≥1 M guanidinium hydrochloride, ≥1 M guanidinium thiocyanate or ≥0.1% sodium dodecyl sulfate or ≥0.1% cetyltrimethylammonium bromide. More specifically, stable associates of precursor proteins are stable in the above solutions for ≥10 min, for example ≥30 min and in particular ≥60 min.

A stable associate is present in particular, if it cannot be dissolved
a) by 0.2 M NaOH inside one hour, and/or
b) by 2 M urea and/or
c) by 1 M guanidinium hydrochloride
inside 10 min, at room temperature (i.e. about 20° C.).

In a further special embodiment, the precursor protein comprises auxiliary sequences (SU) which protect the host cell from damaging influences of the repetitive precursor protein.

In a special embodiment, the precursor protein comprises auxiliary sequences SU which protect the host cell from damaging influences of cationic, antimicrobial peptide sequences present in the repetitive precursor protein. More specifically, these protective sequences comprise negatively charged amino acids (Asp, Glu). More specifically, the auxiliary sequence comprises a number of negatively charged glutamate and/or aspartate amino acids, resulting in an overall net charge at pH=7 of greater than −10 and less than +10, especially greater than −5 and less than +5, for example greater than −2 and less than +2, within the repetitive precursor protein.

In a further special embodiment, the negatively charged protective sequence forms an amphipathic helix. An amphipathic helix according to the present invention is formed if, in the circular arrangement (i.e. in its axial (along the helical axis) projection or top view) of a sequence of 7 consecutive amino acids in the primary structure (A1-A7), in the following order: A1-A5-A2-A6-A3-A7-A4 (FIG. 1), at least 3 adjacent amino acids on said circle are hydrophobic amino acids (Ala, Met, Cys, Phe, Leu, Val, Ile) or glycine, and 3 adjacent amino acids on said circle are hydrophilic amino acids (Thr, Ser, Trp, Tyr, Pro, His, Glu, Gln, Asp, Asn, Lys, Arg) or glycine. This circular arrangement is also referred to as "helical wheel projection".

In a preferred embodiment, the negatively charged protective sequence corresponds to any of the sequences SEQ ID NO: 16-SEQ ID NO: 19.

5. Cleavage Sequences

Cleavage sequences are amino acid sequences which are arranged upstream and downstream of the peptide sequences (Pep) desired according to the invention. These sequences enable the Pep building blocks to be removed from the repetitive precursor protein by "specific" cleavage. In this context, "specific" means that said cleavage occurs in the precursor protein essentially, in particular exclusively, in one or more defined positions, whereby the desired peptide or a precursor thereof is removed.

A "precursor", for example, may consist of a peptide chain which comprises on one end or both ends amino acid residues which are not part of the native, original peptide sequence but which do not interfere with its further use and functionality, or which are removable by cleavage, if required, using conventional chemical or biochemical methods.

Cleavage sequences may act by way of a specific recognition sequence for proteolytically active enzymes which bind to said sequence and cleave the peptide bond between two particular amino acids. Examples are recognition sequences for Arg-C proteinase, Asp-N endopeptidase, caspases, chymotrypsin, clostripain, enterokinase, factor Xa, glutamyl endopeptidase, granzyme B, LysC lysyl endopeptidase (*Achromobacter* proteinase I) LysN Peptidyl-Lys metalloendopeptidase, pepsin, proline endopeptidase, proteinase K, Staphylococcal peptidase I, thermolysin, thrombin, trypsin. The corresponding recognition sequences are described in the literature, for example in Keil, "Specificity of proteolysis" p. 335 Springer-Verlag (1992).

Alternatively, particular amino acid sequences enable the polypeptide backbone to be selectively cleaved by particular chemicals such as, for example, BNPS skatoles (2-(2'-nitrophenylsulfenyl)-3-methyl-3-bromoinolenine), cyanogen bromide, acids, hydroxylamine, iodosobenzoic acid, NTCB (2-nitro-5-thiocyanobenzoic acid).

More specifically, the cleavage sequences used enable the repetitive precursor proteins to be cleaved by chemicals. Particularly suitable cleavage sequences comprise the sequence motifs Asn-Gly, which allows cleavage with hydroxylamine, or Asp-Pro or Asp-Xxx, which allows cleavage with acid, Xxx being any proteinogenic amino acid.

6. Further Developments of Sequences According to the Invention 6.1 Amino Acid Sequences Aside from the sequences for peptides (Pep) specifically disclosed herein, and auxiliary sequences (Aux, SA, SU), repetitive sequences, cleavage sequences and sequences for repetitive precursor proteins, the invention also relates to functional equivalents, functional derivatives and salts of said sequence.

According to the invention, "functional equivalents" mean in particular also mutants which, in at least one sequence position of the abovementioned amino acid sequences, have a different amino acid than the specifically mentioned one but still have the same properties of the originally unmodified peptides. "Functional equivalents" therefore comprise the mutants obtainable by one or more amino acid additions, substitutions, deletions and/or inversions, it being possible for said modifications to occur in any sequence position, as long as they result in a mutant having the property profile according to the invention. More specifically, functional equivalence is present even if the reactivity patterns between mutant and unmodified polypeptide correspond qualitatively.

"Functional equivalents" in the above sense are also "precursors" of the described polypeptides and also "functional derivatives" and "salts" of said polypeptides.

"Precursors" here are natural or synthetic precursors of said polypeptides with or without the desired biological activity.

Examples of suitable amino acid substitutions can be found in the following table:

| Original residue | Substitution examples |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The expression "salts" means both salts of carboxyl groups and acid addition salts of amino groups of the peptide molecules of the invention. Salts of carboxyl groups may be prepared in a manner known per se and comprise inorganic salts such as, for example, sodium, calcium, ammonium, iron and zinc salts, and also salts with organic bases, for example amines such as triethanolamine, arginine, lysine, piperidine and the like. The invention likewise relates to acid addition salts such as, for example, salts with mineral acids such as hydrochloric acid or sulfuric acid, and salts with organic acids such as acetic acid and oxalic acid.

"Functional derivatives" (or "derivatives") of polypeptides according to the invention may likewise be produced on functional amino acid side groups or on the N- or C-terminal end thereof with the aid of known techniques. Examples of derivatives of this kind comprise aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups. Furthermore, from 1 to 5, for example 2, 3 or 4, random D- or L-amino acid residues may additionally be bound covalently (peptidically) to the N- and/or C-terminals.

6.2 Nucleic Acids, Expression Construction, Vectors and Microorganisms Comprising Them Nucleic Acids The invention furthermore comprises the nucleic acid molecules coding for the peptide and protein sequences employed according to the invention.

All of the nucleic acid sequences mentioned herein (single- and double-stranded DNA and RNA sequences, for example cDNA and mRNA) may be prepared in a manner known per se by chemical synthesis from the nucleotide building blocks, for example by fragment fusion of individual overlapping, complementary nucleic acid building blocks of the double helix. For example, oligonucleotides may be chemically synthesized in the known manner by the phosphoamidite method (Voet, Voet, 2nd edition, Wiley Press New York, pages 896-897). Assembling synthetic oligonucleotides and filling-in gaps with the aid of the Klenow fragment of DNA polymerase and ligation reactions as well as general cloning methods are described in Sambrook et al. (1989), Molecular Cloning: A laboratory manual, Cold Spring Harbor Laboratory Press.

The invention relates to both isolated nucleic acid molecules which code for polypeptides or proteins according to the invention or biologically active segments thereof, and nucleic acid fragments which may be used, for example, as hybridization probes or primers for identifying or amplifying coding nucleic acids according to the invention.

The nucleic acid molecules according to the invention may moreover comprise untranslated sequences from the 3'- and/or 5' ends of the coding gene region.

An "isolated" nucleic acid molecule is removed from other nucleic acid molecules present in the natural source of said nucleic acid and additionally may be essentially free of other cellular material or culture medium when prepared by recombinant techniques, or free of chemical precursors or other chemicals when synthesized chemically.

A nucleic acid molecule according to the invention may be isolated by means of standard molecular-biological techniques and the sequence information provided according to the invention. For example, cDNA may be isolated from a suitable cDNA library by using any of the specifically disclosed concrete sequences or any segment thereof as hybridization probe and standard hybridization techniques (as described, for example, in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). Moreover, a nucleic acid molecule comprising any of the disclosed sequences or a segment thereof, isolated by polymerase chain reaction using the oligonucleotide primers generated based on this sequence, can be used. The nucleic acids amplified in this way may be cloned into a suitable vector and characterized by DNA sequence analysis. The oligonucleotides according to the invention may also be prepared by standard synthesis methods, for example using a DNA synthesizer.

The invention furthermore comprises the nucleic acid molecules complementary to the specifically described nucleotide sequences or a segment thereof.

The nucleotide sequences according to the invention enable probes and primers to be generated which can be used for identifying and/or cloning homologous sequences in other cell types and organisms. Such probes and primers commonly comprise a nucleotide sequence region which hybridizes to at least about 12, preferably at least about 25, for example about 40, 50 or 75, consecutive nucleotides of a sense strand of a nucleic acid sequence according to the invention or of a corresponding antisense strand, under stringent conditions.

The invention also comprises those nucleic acid sequences which comprise "silent mutations" or which have been modified compared to a specifically mentioned sequence according to the codon usage of a special original or host organism, as well as naturally occurring variants such as, for example, splice variants or allele variants thereof. The invention also relates to sequences obtainable by conservative nucleotide substitutions (i.e. the amino acid in question is replaced with an amino acid of equal charge, size, polarity and/or solubility).

The invention also relates to molecules derived from the specifically disclosed nucleic acids due to sequence polymorphisms. These genetic polymorphisms may exist among individuals within a single population owing to natural variation. These natural variations usually result in a variance of from 1 to 5% in the nucleotide sequence of a gene.

The invention furthermore also comprises nucleic acid sequences which hybridize to abovementioned coding sequences or are complementary thereto. These polynucleotides can be found by screening genomic or cDNA libraries and optionally be amplified therefrom by means of PCR using suitable primers and then be isolated, for example, using suitable probes. Another possibility is that of transforming suitable microorganisms with polynucleotides or vectors according to the invention, propagating said microorganisms and therefore said polynucleotides and subsequently isolating them. In addition, polynucleotides according to the invention may also be synthesized chemically.

The property of being able to "hybridize" to polynucleotides means the ability of a poly- or oligonucleotide to bind to a virtually complementary sequence under stringent conditions, while unspecific binding reactions between non-complementary partners do not occur under these conditions. For this purpose, the sequences should be 70-100%, preferably 90-100%, complementary. The property of complementary sequences of being able to specifically bind to one another is utilized, for example, in the Northern or Southern blot technique or with primer binding in PCR or RT-PCR. Usually, oligonucleotides of at least 30 base pairs in length are employed for this purpose. Stringent conditions mean, for example, in the Northern blot technique, using a 50-70° C., preferably 60-65° C. washing solution, for example 0.1×SSC buffer containing 0.1% SDS (20×SSC: 3 M NaCl, 0.3 M sodium citrate, pH 7.0) to elute unspecifically hybridized cDNA probes or oligonucleotides. As mentioned above, only highly complementary nucleic acids remain attached to one another in this case. Adjusting stringent conditions is known to the skilled worker and described, for example, in Ausubel et al., Current Protocols in Molecular Biology, John Wiley & Sons, N.Y. (1989), 6.3.1-6.3.6.

"Identity" between two nucleic acids means the identity of the nucleotides over in each case the entire length of the nucleic acids, in particular the identity calculated by way of comparison with the aid of the Vector NTI Suite 7.1 Software from Informax (USA) and applying the Clustal method (Higgins D G, Sharp P M. Fast and sensitive multiple sequence alignments on a microcomputer. Comput Appl. Biosci. 1989 April; 5(2):151-1), and setting the following parameters:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Expression Constructs and Vectors:

The invention additionally relates to expression constructs comprising a nucleic acid sequence coding for a peptide or precursor protein according to the invention under genetic control by regulatory nucleic acid sequences, and to vectors comprising at least one of said expression constructs. Such constructs according to the invention preferably comprise a promoter 5' upstream of the particular coding sequence, and a terminator sequence 3' downstream, and optionally further common regulatory elements which in each case are operatively linked to the coding sequence. "Operative linkage" means the sequential arrangement of promoter, coding sequence, terminator and optionally further regulatory elements in such a way that each of said regulatory elements can carry out its intended function during expression of the coding sequence. Examples of operatively linkable sequences are targeting sequences and also enhancers, polyadenylation signals and the like. Further regulatory elements comprise selectable markers, amplification signals, origins of replication and the like. Suitable regulatory sequences are described, for example, in Goeddel, Gene Expression Technology: Methods in Enzymology 185, Academic Press, San Diego, Calif. (1990).

The natural regulatory sequence may still be present upstream of the actual structural gene, in addition to the artificial regulatory sequences. This natural regulation may optionally be switched off by genetic modification, thereby increasing or reducing expression of the genes. However, the gene construct may also have a simpler structure, i.e. no additional regulatory signals are inserted upstream of the structure gene, and the natural promoter with its regulation is not removed. Instead, the natural regulatory sequence is mutated in such a way that regulation no longer takes place and gene expression is increased or reduced. The gene construct may comprise one or more copies of the nucleic acid sequences.

Examples of usable promoters are: cos, tac, trp, tet, trp-tet, lpp, lac, lpp-lac, lacIq, T7, T5, T3, gal, trc, ara, SP6, lambda-PR or in lambda-PL promoter, which are advantageously used in gram-negative bacteria; and also the gram-positive promoters amy and SPO$_2$, the yeast promoters ADC1, MFa, AC, P-60, CYC1, GAPDH, or the plant promoters CaMV/35S, SSU, OCS, lib4, usp, STLS1, B33, not, or the ubiquitin promoter or phaseolin promoter. Particular preference is given to using inducible promoters such as, for example, light- and particularly temperature-inducible promoters such as the P$_r$P$_l$ promoter. In principle, any natural promoters with their regulatory sequences may be used. In addition, synthetic promoters may also be used advantageously.

Said regulatory sequences are intended to enable the nucleic acid sequences and the proteins to be expressed in a specific manner. Depending on the host organism, this may mean that the gene is expressed or overexpressed only after induction or that it is expressed and/or overexpressed immediately, for example.

Preference is given here to the regulatory sequences or factors being able to positively influence and thereby increase or reduce expression. Thus it is possible for the regulatory elements to be enhanced advantageously at the transcriptional level by using strong transcription signals such as promoters and/or "enhancers". In addition, however, it is also possible to enhance translation, for example by improving the stability of mRNA.

An expression cassette is prepared by fusing a suitable promoter to a suitable coding nucleotide sequence and to a termination or polyadenylation signal. For this purpose, familiar recombination and cloning techniques are used, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

To express the recombinant nucleic acid construct or gene construct in a suitable host organism, it is advantageously inserted into a host-specific vector which enables the genes to be optimally expressed in the host. Vectors are well known to the skilled worker and can be found, for example, in "Cloning Vectors" (Pouwels P. H. et al., eds., Elsevier, Amsterdam-New York-Oxford, 1985). Vectors are understood to include in addition to plasmids also any other vectors known to the skilled worker, such as phages, viruses such as SV40, CMV, baculovirus and adenovirus, transposons, IS elements, plasmids, cosmids, and linear or circular DNA, for example. Said vectors may be replicated autonomously in the host organism or chromosomally.

Examples of suitable expression vectors which may be mentioned are:

Common fusion expression vectors such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.), in which glutathione S transferase (GST), maltose E-binding protein and protein A, respectively, are fused to the recombinant target protein.

Non-fusion protein expression vectors such as pTrc (Amann et al., (1988) Gene 69:301-315) and pET 11d (Studier et al. Gene Expression Technology: Methods in Enzymology 185, Academic Press, San Diego, Calif. (1990) 60-89).

Yeast expression vector for expression in *S. cerevisiae* yeast, such as pYepSec1 (Baldari et al., (1987) Embo J. 6:229-234), pMFa (Kurjan and Herskowitz (1982) Cell 30:933-943), pJRY88 (Schultz et al., (1987) Gene 54:113-123) and pYES2 (Invitrogen Corporation, San Diego, Calif.). Vectors and methods of constructing vectors suitable for use in other fungi such as filamentous fungi, comprise those that are described in detail in: van den Hondel, C. A. M. J. J. & Punt, P. J. (1991) "Gene transfer systems and vector development for filamentous fungi", in: Applied Molecular Genetics of Fungi, J. F. Peberdy et al., eds., pp. 1-28, Cambridge University Press: Cambridge.

Baculovirus vectors available for expressing proteins in cultured insect cells (for example Sf9 cells) comprise the pAc series (Smith et al., (1983) Mol. Cell. Biol. 3:2156-2165) and the pVL series (Lucklow and Summers, (1989) Virology 170:31-39).

Plant expression vectors such as those described in detail in: Becker, D., Kemper, E., Schell, J. and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721.

Mammalian expression vectors such as pCDM8 (Seed, B. (1987) Nature 329:840) and pMT2PC (Kaufman et al. (1987) EMBO J. 6:187-195).

Other suitable expression systems for prokaryotic and eukaryotic cells are described in chapters 16 and 17 of Sambrook, J., Fritsch, E. F. and Maniatis, T., Molecular cloning: A Laboratory Manual, 2nd edition, Cold Spring Harbor Laboratory, Cold Spring Harbor Laboratory Press, Cold Spring Harbor, N.Y., 1989.

Recombinant Microorganisms:

It is possible to produce with the aid of the vectors according to the invention recombinant microorganisms which have been transformed, for example, with at least one vector according to the invention and which may be employed for producing the polypeptides according to the invention. Advantageously, the above-described recombinant constructs according to the invention are introduced into a suitable host system and expressed. Preference is given here to using cloning and transfection methods familiar to the skilled worker, such as coprecipitation, protoplast fusion, electroporation, retroviral transfection and the like, for example, in order to bring about expression of said nucleic acids in the respective expression system. Suitable systems are described, for example, in Current Protocols in Molecular Biology, F. Ausubel et al., Hrsg., Wiley Interscience, New York 1997, or Sambrook et al., Molecular Cloning: A Laboratory Manual. 2nd ed., Cold Spring Harbor Laboratory, Cold Spring Harbor Laboratory Press, Cold Spring Harbor, N.Y., 1989.

According to the invention, it is also possible to produce homologously recombined microorganisms. For this purpose, a vector is prepared which comprises at least one segment of a gene according to the invention or of a coding sequence, into which optionally at least one amino acid deletion, addition or substitution has been introduced in order to modify, for example to functionally disrupt ("knockout" vector), the sequence according to the invention. The introduced sequence may also be, for example, a homolog from a related microorganism or derived from a mammalian, yeast or insect source. The vector used for homologous recombination may alternatively be designed in such a way that upon homologous recombination the endogenous gene is mutated or modified in another way but still encodes the functional protein (for example, the upstream regulatory region may have been modified in such a way that this alters the expression of the endogenous protein). The modified segment of the gene according to the invention is present in the homologous recombination vector. The construction of suitable vectors for homologous recombination is described, for example, in Thomas, K. R. and Capecchi, M. R. (1987) Cell 51:503.

Suitable host organisms are in principle any organisms that enable the nucleic acids according to the invention, their allelic variants, their functional equivalents or derivatives to be expressed. Host organisms mean, for example, bacteria, fungi, yeasts, plant or animal cells.

Non-limiting examples of prokaryotic expression organisms are *Escherichia coli, Bacillus subtilis, Bacillus megaterium, Corynebacterium glutamicum*, and others. Non-limiting examples of eukaryotic expression organisms are yeasts such as *Saccharomyces cerevisiae, Pichia pastoris*, and others, filamentous fungi such as *Aspergillus niger, Aspergillus oryzae, Aspergillus nidulans, Trichoderma reesei, Acremonium chrysogenum*, and others, mammalian cells such as Hela cells, COS cells, CHO cells, and others, insect cells such as Sf9 cells, MEL cells, and others, plants or plant cells such as *Solanum tuberosum, Nicotiana*, and others.

Successfully transformed organisms may be selected by means of marker genes which are likewise present in the vector or in the expression cassette. Examples of such marker genes are genes for resistance to antibiotics and for enzymes catalyzing a coloring reaction which results in staining of the transformed cells. The latter may then be selected by means of automated cell sorting. Microorganisms successfully transformed with a vector, which carry an appropriate antibiotic resistance gene (e.g. G418 or hygromycin), can be selected by means of liquid or solid culture media comprising corresponding antibiotics. Marker proteins presented on the cell surface may be utilized for selection by means of affinity chromatography.

7. Recombinant Production of Precursor Proteins and Peptides

The peptides and precursor proteins used according to the invention may in principle be produced recombinantly in a manner known per se, which involves culturing a peptide/precursor protein-producing microorganism, optionally inducing expression of said polypeptides and isolating the latter from the culture. In this way it is also possible to produce the peptides and precursor proteins on an industrial scale, if desired.

The recombinant microorganism may be cultured and fermented according to known methods. For example, bacteria may be propagated in TB or LB medium and at from 20 to 40° C. and pH 6 to 9. Suitable culturing conditions are described in detail, for example, in T. Maniatis, E. F. Fritsch and J. Sambrook, Molecular Cloning: A Laboratory Manual, Cold Spring Harbor Laboratory, Cold Spring Harbor, N.Y. (1989).

Unless the peptides or precursor proteins are secreted into the culture medium, the cells are then disrupted and the product is recovered from the lysate by known protein isolation methods. The cells may optionally be disrupted by high-frequency ultrasound, by high pressure, for example in a French pressure cell, by osmolysis, by the action of detergents, lytic enzymes or organic solvents, by homogenizers, or by combining a plurality of the methods listed.

The peptides or precursor proteins may be purified using known, chromatographic methods such as molecular sieve chromatography (gel filtration) such as Q-Sepharose chromatography, ion exchange chromatography, and hydrophobic chromatography, and by other common methods such as ultrafiltration, crystallization, salting out, dialysis and native gel electrophoresis. Suitable methods are described, for example, in Cooper, F. G., Biochemische Arbeitsmethoden [original title: The Tools of Biochemistry], Verlag Walter de Gruyter, Berlin, N.Y. or in Scopes, R., Protein Purification, Springer Verlag, New York, Heidelberg, Berlin.

Furthermore, the recombinant peptide or precursor protein may be isolated by using vector systems or oligonucleotides which extend the cDNA by particular nucleotide sequences and therefore code for modified polypeptides or fusion proteins which are used for simpler purification, for example. Examples of suitable modifications of this kind are "tags" acting as anchors, for example the modification known as hexa-histidine anchor, or epitopes that can be recognized as antigens by antibodies (described, for example, in Harlow, E. and Lane, D., 1988, Antibodies: A Laboratory Manual. Cold Spring Harbor (N.Y.) Press). These anchors may be used for fixing the proteins to a solid support such as, for example, a polymer matrix which may be introduced, for example, into a chromatographic column or may be used on a microtiter plate or another support.

At the same time, these anchors may also be used for recognizing the proteins. The proteins may moreover be recognized by using common markers such as fluorescent dyes, enzyme markers forming a detectable reaction product upon reaction of a substrate, or radioactive markers, either alone or in combination with said anchors, in order to derivatize the proteins.

More specifically, the repetitive precursor proteins are produced by expressing synthetically prepared gene sequences which code for the repetitive precursor proteins according to the invention. One possible preparation of synthetic gene sequences is described in Hummerich et al. Biochemistry 43; 13604-13612 (2004).

The repetitive precursor proteins may be present in the host cell in a soluble or insoluble form. In both cases, the cells are disrupted. More specifically, disruption is carried out by means of a high pressure homogenizer at 1000-1500 bar. With soluble repetitive precursor proteins, a large part of the cellular proteins is precipitated by heating the lysate to 60-100° C., such as 70-90° C. or 75-85° C. and removed from the soluble repetitive precursor protein by a suitable separation method (e.g. sedimentation or filtration). The repetitive precursor protein is then precipitated by adding a cosmotropic salt (as described above). The repetitive precursor proteins form stable associates in the process. Depending on the associate, the final concentrations of the cosmotropic salts added may vary and are approximately in a range from about 0.2-3 M or e.g. 0.8-2 M. Optimal concentrations can be determined in a simple manner familiar to the protein chemist.

The repetitive precursor proteins may also be assembled without an external trigger. In this case, the repetitive precursor proteins already assemble in the host cell to give corresponding stable associates. After disruption of the cells, said associates are separated from soluble components by a suitable separation method (e.g. sedimentation or filtration).

Removal of the associates may be improved by adding auxiliary precipitants after disruption of the cells. Said auxiliary precipitants cause further clotting of the associates, as a result of which lower accelerations are required for sedimentation, for example, in order to separate the associates from the aqueous medium. Auxiliary precipitants which may be used are acids, lyes, polymer solutions, in particular aqueous solutions of charged polymers. Examples of auxiliary precipitants are phosphoric acid or polyethyleneimine solutions.

The stable associates of repetitive precursor proteins may be purified further. For this purpose, solutions in which the stable associates are insoluble but other contaminations are solved are used for this purification. More specifically, aqueous solutions of bases, acids, urea, salts and detergents are used. Particularly suitable is the use of solutions of alkali metal hydroxides, urea, guanidinium salts or charged detergents such as, for example, alkyltrimethylammonium salts or alkyl sulfates. More specifically, use is made of solutions of ≥0.2 M sodium hydroxide, ≥2 M urea, ≥1 M guanidinium hydrochloride, ≥1 M guanidinium thiocyanate or ≥0.1% sodium dodecyl sulfate or ≥0.1% cetyltrimethylammonium bromide. For purification, the stable associates are resuspended in the corresponding solutions and then separated from the solution by a simple separation method (for example sedimentation or filtration). The repetitive precursor proteins are then washed with water and dried using methods familiar to the skilled worker.

In order to recover the peptides from the repetitive precursor proteins, these sequences must be cleaved out of said precursor proteins and separated from the auxiliary sequences. Cleavage takes place at the cleavage sequences present in the repetitive precursor proteins. Methods for specific cleavage of amino acid chains are described in the literature. Repetitive precursor proteins may be cleaved enzymatically or chemically. Examples of enzymes which may be used for specifically cleaving amino acid chains are Arg-C proteinase, Asp-N endopeptidase, caspases, chymotrypsine, clostripain, enterokinase, factor Xa, glutamylendo peptidase, granzyme B, LysC lysylendo peptidase (Achromobacter proteinase I) LysN Peptidyl-Lys metalloendo peptidase, pepsin, proline endopeptidase, proteinase K, staphylococcal peptidase I, thermolysine, thrombin, trypsine. Examples of chemicals which may be used for specifically cleaving amino acid chains are BNPS-skatole (2-(2'-nitrophenylsulfenyl)-3-methyl-3-bromoinolenine), bromcyane, acids, hydroxylamine, iodosobenzoic acid, NTCB (2-nitro-5-thiocyanobenzoic acid).

More specifically, repetitive precursor proteins are cleaved chemically, for example by cleavage with hydroxylamine or acid. Any inorganic or organic acid having a $pK_s$ of less than 5 and greater than 0, preferably less than 4 and greater than 1, is suitable for acidic cleavage. More specifically, 1-5% phosphoric acid or 1-5% formic acid is used for said cleavage. Depending on the conditions of acidic cleavage, either a simple cleavage that takes place between the amino acids Asp and Pro or Asp and Xxx, Xxx being any proteinogenic amino acid, or first a cleavage occurs between the amino acids Asp and Pro or Asp and Xxx and then the aspartate is completely cleaved off the amino acid N-terminally upstream of said aspartate in the amino acid sequence of the peptide.

Cleavage may be carried out using the purified repetitive precursor protein or using a cellular fraction comprising the repetitive precursor protein (e.g. soluble components of the host cell or insoluble components of a host cell), or using intact host cells comprising the repetitive precursor protein. The cleaving agent must be inactivated after cleavage. Methods for this purpose are known to the skilled worker.

After inactivation, the cleavage reaction mixture comprises inter alia the desired peptide, cleaved-off auxiliary sequences and inactivated cleaving agents. In this solution, the peptides may already have their desired activity. If greater purity is required, the peptides liberated from the repetitive precursor proteins may be removed from the auxiliary sequences after cleavage. An advantage of the self-assembling auxiliary sequences is the fact that said auxiliary sequences assemble during or after cleavage. They may either assemble spontaneously during cleavage under the chosen cleavage conditions or due to the addition of substances supporting the assembling of said auxiliary sequences. Such assembling-promoting substances are, for example, cosmotropic salts comprising at least one type of ion that has more cosmotropic properties than sodium or chloride ions, according to the Hofmeister series. Other assembling-promoting substances are acids or lyes or organic solvents miscible with water, such as alcohols, for example. The assembled auxiliary sequences may be removed from the soluble liberated peptide by sedimentation or filtration. Further purification steps may be required in order to remove remaining protein or peptide contaminations or salts or other substances added during or after cleavage from the desired peptide. For this purpose, for example, chromatographic methods, precipitations, dialysis, two-phase extractions and other methods familiar to the skilled worker may be employed.

The peptide-containing solution may then be employed directly for the desired application, or the solution may be dried using methods familiar to the skilled worker (e.g. spray drying or freeze drying), with the corresponding dry product being used.

After drying, it is possible to remove contaminations which cannot be removed from the peptide, as long as the latter is dissolved in water, by washing with solvents in which said peptide is insoluble. Suitable for this are organic solvents such as, for example, n-hexane, N-methylpyrrolidone, or mixtures of solvents and acids such as, for example, mixtures of n-hexane and acetic acid, or organic acids such as, for example, acetic acid or hexanoic acid. For this purification step, the dried peptide is resuspended in the appropriate solvent/solvent mixture and then removed again by sedimentation or filtration. Residual solvent/solvent mixture may be removed by drying.

The desired peptides in the form obtained by cleavage may have the desired activity. However, it may also be necessary to further modify the peptides after cleavage. For example, the peptide may be amidated, esterified, oxidized, alkylated or chemically linked to any molecules. Examples of molecules which may be used for such modifications are alcohols, alcohol cysteine esters, carboxylic acids, thioesters or maleimides. More particularly, molecules used for such modifications are those which increase the hydrophobicity of the peptide. Such molecules may comprise modified or unmodified alkyl radicals, as defined above. Such molecules preferably comprise $C_2$-$C_{16}$-, in particular $C_6$-$C_{14}$-alkyl radicals. Corresponding methods are known to the skilled worker. The modification may be carried out at any time: for example directly after cell disruption, after purification of the precursor protein, after cleavage of the precursor protein, or after purification of the peptide.

Peptide solutions having the desired degree of purity may be used directly. Alternatively, different preservation methods may be applied for longer-term storage. Examples of preservation methods are cooling, freezing, addition of preservatives. Alternatively, the peptides may be dried. Examples of drying methods are lyophilization or spray drying. Dried peptides may then be stored. In order to use the peptides, the dried substance is dissolved in a suitable solvent, preferably an aqueous solution. Said aqueous solution may comprise salts or buffer substances or no further additions.

8. Definition of Various Other General Terms

Unless stated otherwise, a sequence "derived" from a specifically disclosed sequence or "homologous" thereto, for example a derived amino acid or nucleic acid sequence, means according to the invention a sequence which is at least 80% or at least 90%, in particular 91%, 92%, 93%, 94%, 95%, 96%, 97%, 98% and 99%, identical to the starting sequence.

EXPERIMENTAL SECTION

The universal applicability of the method described in the present invention of producing any peptide sequences (Pep) is demonstrated on the basis of producing three peptides with different sequences and amino acid compositions (ZnO, P18, Min).

Unless stated otherwise, standard methods of organic and biochemical analysis and of recombinant production of proteins and cultivation of microorganisms are used.

Example 1

Production of Peptide ZnO (SEQ ID NO:20)

The peptide ZnO is a peptide derived from a published sequence, which influences the formation of zinc oxide particles (Umetsu et al. Adv. Mat. 17: 2571-75 (2005)). A synthetic gene, $ZnO_4$ (SEQ ID NO:21), was cloned into the vector pAZL described in Hummerich et al. Biochemistry 43; 13604-13612 (2004), using the restriction endonucleases BamHI and HindIII, and dimerized according to the protocol described there, and cloned into the vector pET21 (Novagen). The sequence is subsequently present in said vector codes for the repetitive precursor protein $ZnO_8$ (SEQ ID NO:22). Said repetitive precursor protein comprises 8 repeats, each of which comprises a copy of the ZnO peptide and an auxiliary sequence. Said auxiliary sequence comprises a poly-alanine sequence and imparts self-assembling properties to the repetitive precursor protein. The amino acids Asp-Pro which are intended to enable the ZnO peptide to be selectively cleaved out of the precursor protein using acids are located between the auxiliary sequences and the peptide sequences. The expression was carried out in the strain *E. coli* BL21 [DE3] (Novagen).

Cultivation and protein synthesis were carried out at $pO_2>20\%$ and pH=6.8 in a fed batch process.

Medium:

| | | |
|---|---|---|
| 8 liters | Water | |
| 25 g | Citric acid monohydrate | |
| 40 g | Glycerol (99%) | |
| 125 g | Potassium dihydrogen phosphate ($KH_2PO_4$) | |
| 62.5 g | Ammonium sulfate (($NH_4)_2SO_4$) | |
| 18.8 g | Magnesium sulfate heptahydrate ($MgSO_4 * 7\ H_2O$) | |
| 1.3 g | Calcium chloride dihydrate ($CaCl_2 * 2\ H_2O$) | |
| 155 ml | Trace salt solution | |
| | Add water to 9.8 liter | |
| | Adjust pH with 25% strength NaOH to 6.3 | |
| 3 ml | Tego KS 911 (antifoam; Goldschmidt Produkte) | |
| 1 g | Ampicillin | |
| 190 mg | Thiamine hydrochloride | |
| 20 mg | Vitamin B12 | |

Trace Salt Solution:

| | |
|---|---|
| 5 liter | Water |
| 200.00 g | Citric acid monohydrate |
| 55.00 g | $ZnSO_4 * 7\ H_2O$ |
| 42.50 g | $(NH_4)_2Fe(SO_4)_2 * 6\ H_2O$ |
| 15.00 g | $MnSO_4 * H_2O$ |
| 4.00 g | $CuSO_4 * 5\ H_2O$ |
| 1.25 g | $CoSO_4 * 7\ H_2O$ |

Feeding Solution:

| | |
|---|---|
| 1125 g | Water |
| 41.3 g | Citric acid monohydrate |
| 81.6 g | Sodium sulfate ($Na_2SO_4$) |
| 6.3 g | $(NH_4)_2Fe(SO_4)_2 * 6\ H_2O$ |
| 4734 g | Glycerol 99.5% |

After the glycerol present in the basic medium had been exhausted, a constant feed at a rate of 100 ml/h was started.

Protein synthesis was induced by adding 1 mM isopropyl β-D-thiogalactopyranoside, after the bacterial culture had reached an optical density of $OD_{600}=60$. At this point, the temperature of the culture was lowered from 37° C. to 30° C. The cells were harvested 5 h after induction.

$ZnO_8$ was purified according to the following protocol:
Resuspension of the cell pellet in 5 ml of 20 mM MOPS (3-(N-morpholino)propanesulfonic acid) pH 7.0 per gram of wet mass
Disruption of the cells in a high pressure homogenizer at 1400 bar
Centrifugation, 30 min at 5000×g
Incubation of the supernatant, 30 min at 80° C.
Centrifugation, 30 min at 5000×g
Precipitation of $ZnO_8$ from the supernatant by adding 1.8 M ammonium sulfate (final concentration) at 4° C. overnight
Washing of the pellet with 8 M urea
2× washing of the pellet with water
Lyophilization
The lyophilized $ZnO_8$ was brought to −20° C.

From each liter of culture medium, 2.2 g of pure $ZnO_8$ were recovered.

For cleavage, 250 mg of the lyophilized $ZnO_8$ precursor protein were resuspended in 5 ml of 1% formic acid and incubated at 90° C. for 6 h. During this incubation the lyophilisate dissolved, resulting in a gel-like substance. After cooling to room temperature, the gel-like substance was removed from the soluble components by sedimentation at 18000×g. The remaining solution was neutralized with 2 M NaOH. The solution was then lyophilized. The lyophilisate comprised the desired cleavage product and sodium formate from neutralization of the formic acid.

Figure 2:
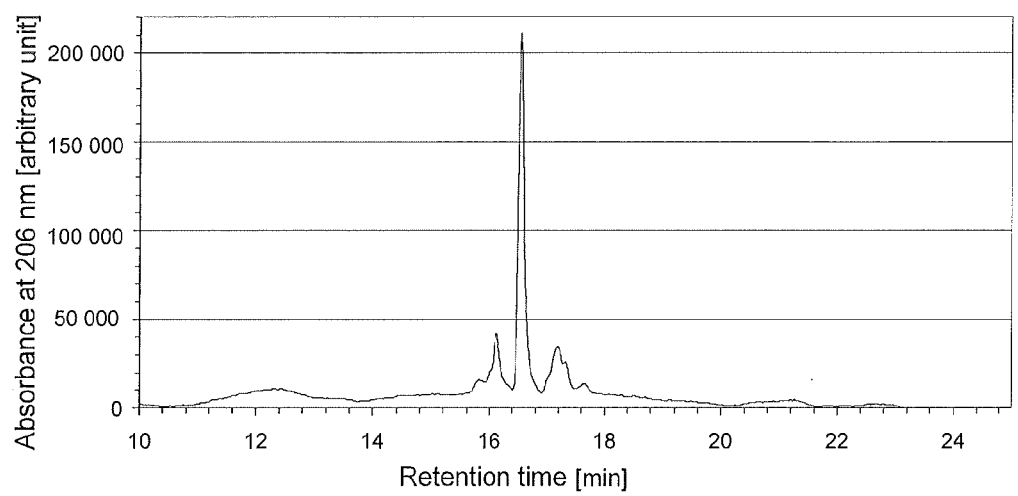
FIG. 2 depicts the reversed phase chromatogram of the peptide "ZnO" after acidic cleavage.
Figure 3:
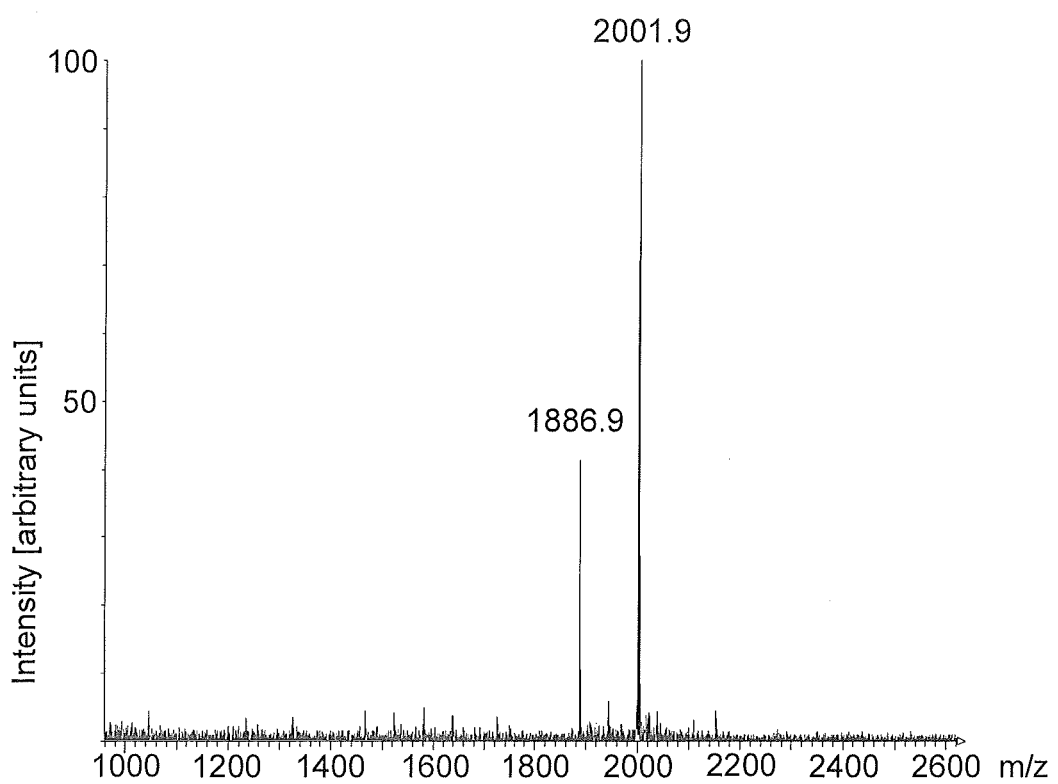
FIG. 3 depicts the mass spectrum of the "ZnO" peptide after acidic cleavage and reversed phase HPLC; the numbers shown indicate the m/z value of the particular monoisotopic peak.

The lyophilized product was analyzed by means of HPLC: for this, the product was dissolved at a concentration of 1 mg/ml in water and analyzed using a reversed phase chromatographic column (Jupiter Proteo 4.6×250 mm; Phenomenex). The eluent used was 0.1% trifluoroacetic acid in water, which was replaced with 0.1% trifluoroacetic acid in acetonitrole, using a linear gradient. Detection was carried out at 206 nm (FIG. 2). For further analysis, the fractions of the main peak were collected and the substance present therein was studied further. N-terminal sequencing confirmed that this component is the ZnO peptide. Studies by means of mass spectrometry (MALDI-TOF) established a mass of 2002, which is identical to the theoretical mass of the ZnO peptide (FIG. 3). HPLC analysis revealed a purity of 62% based on UV-active components.

Example 2

Production of Peptide P18 (SEQ ID NO: 23)

Peptide P18 is a peptide derived from a highly active antimicrobial peptide sequence described by Shin et al. J. Peptide Res. 58:504-14 (2001). A synthetic gene, AHeAP18$_2$ (SEQ ID NO:24), was cloned into the vector pAZL described in Hummerich et al. Biochemistry 43; 13604-13612 (2004), using the restriction endonucleases BamHI and HindIII, and dimerized according to the protocol described there, and cloned into the vector pET21 (Novagen). The sequence subsequently present in said vector codes for the repetitive precursor protein AHeAP18$_4$ (SEQ ID NO:25). Said repetitive precursor protein comprises 4 repeats, each of which comprises a copy of the P18 peptide and an auxiliary sequence. Said auxiliary sequence comprises two poly-alanine sequences and imparts self-assembling properties to the repetitive precursor protein. Moreover, the auxiliary sequence comprises a negatively charged helical protective sequence. The amino acids Asp-Pro which are intended to enable the P18 peptide to be selectively cleaved out of the precursor protein by acids are located between the auxiliary sequences and the P18 peptide sequences. The expression was carried out in the strain *E. coli* BL21 [DE3] (Novagen).

Cultivation and protein synthesis were carried out in a fed batch process at pO$_2$>20% and pH=6.8. Medium, trace salt solution and feeding solution had the composition described in example 1.

After the glycerol present in the basic medium had been exhausted, a constant feed at a rate of 100 ml/h was started.

Protein synthesis was induced by adding 1 mM isopropyl β-D-thiogalactopyranoside, after the bacterial culture had reached an optical density of OD$_{600}$=60. 10 h after induction, the cells were harvested by sedimentation at 5000×g for 30 min. The wet biomass was 1932 g.

Figure 4:
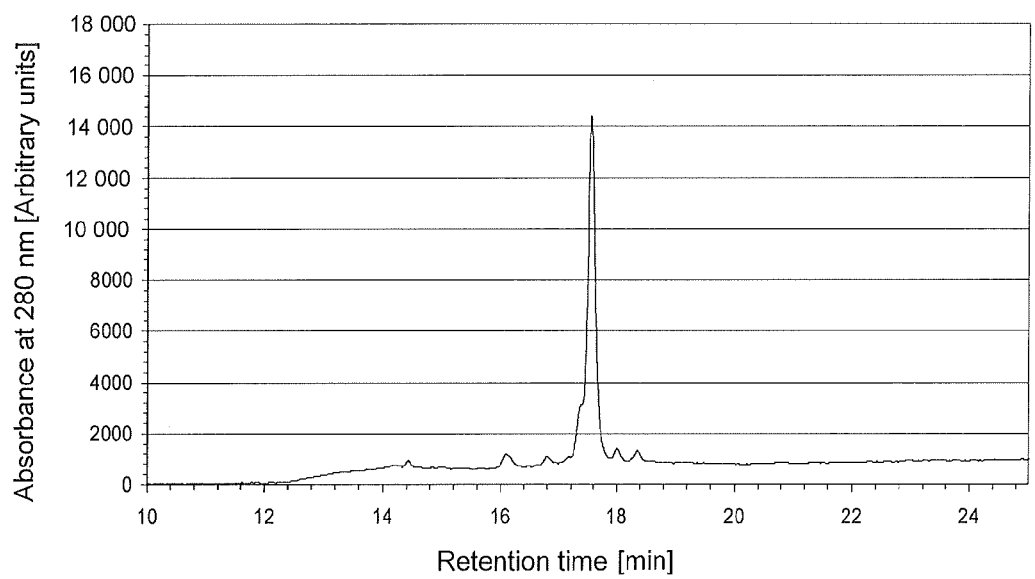
FIG. 4 depicts the reversed phase chromatogram of the peptide "P18" after acidic cleavage and cation exchange chromatography.

The wet biomass was purified according to the following protocol:
Resuspension of the cell pellet: for each g of biomass, 6 g of 20 mM sodium phosphate buffer (pH 7.5) were added and mixed thoroughly.
Disruption of the cells in a high pressure homogenizer at 1500 bar
Addition of phosphoric acid to pH=3±0.5
10 min incubation at 23° C. with stirring
Centrifugation: 20 min, at least 5000×g
Resuspension of the pellet: for each g of wet mass add 25 ml of 0.2 M NaOH, homogenize and incubate with stirring at 23° C. for 4 hours
Neutralization: adjust pH of 8.5±0.5 with 85% strength H$_3$PO$_4$
Centrifugation: 20 min, at least 5000×g
The pellet consisting of washed inclusion bodies comprising the P18 precursor protein was hydrolyzed or cleaved by means of 2% strength H$_3$PO$_4$.
  Cleavage Conditions:
    i. use 5 ml of H$_3$PO$_4$ for each g of pellet
    ii. homogenize
    iii. incubate with shaking at 90° C. for 16 hours.
Let cleavage reaction mixture cool down.
Centrifugation: 20 min, at least 5000×g
Neutralization: adjust pH of 5.5±0.5 with 10 M NaOH
Centrifugation: 20 min, at least 5000×g
Dilute supernatant with water until conductivity less than 10 mS/cm
Purify P18 from supernatant via cation exchange chromatography (Fractogel COO; Merck); elution with 450 mM NaCl
Pool peptide-containing fractions and dilute with water until conductivity is less than 10 mS/cm
Purify P18 from pooled fractions via cation exchange chromatography (Fractogel COO; Merck); elution with 50 mM HCl The eluate was neutralized with 2 M NaOH.
The neutralized solution was lyophilized.
The lyophilized product was analyzed by means of HPLC: for this, the product was dissolved at a concentration of 1 mg/ml in water and analyzed using a reversed phase chromatographic column (Jupiter Proteo 4.6×250 mm; Phenomenex). The eluent used was 0.1% trifluoroacetic acid in water, which was replaced with 0.1% trifluoroacetic acid in acetonitrole, using a linear gradient. Detection was carried out at 280 nm (FIG. 4). For further analysis, the fractions of the main peak were collected and the substance present therein was studied further. N-terminal sequencing confirmed that this component is the P18 peptide.

Figure 5:
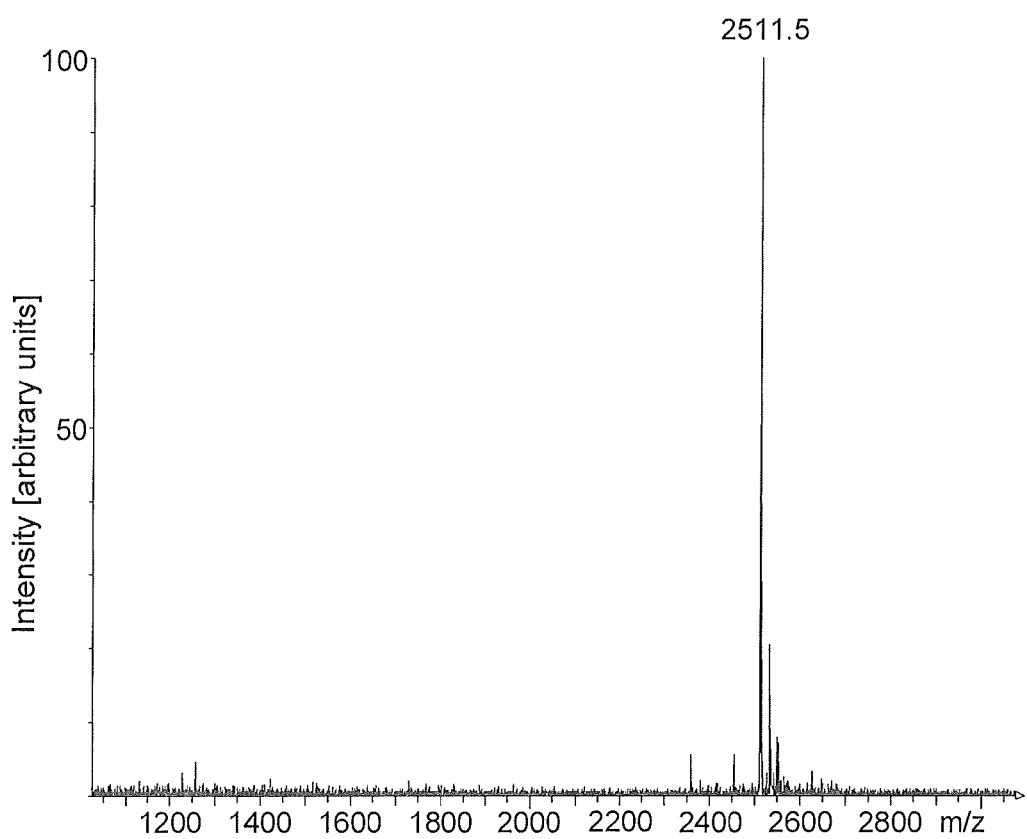
FIG. 5 depicts the mass spectrum of the "P18" peptide after acidic cleavage, cation exchange chromatography and reversed phase HPLC; the numbers shown indicate the m/z value of the particular monoisotopic peak.

Studies by means of mass spectrometry (MALDI-TOF) established a mass of 2512 for the peptide, which is identical to the theoretical mass of the P18 peptide (FIG. 5). HPLC analysis revealed a purity of 85% based on UV-active components. From 30 g of wet biomass, 52 mg of P18 peptide were obtained. Therefore, approx. 330 mg of pure P18 peptide can be recovered from each liter of fermentation culture.

To investigate the activity of the P18 peptide, *E. coli* B cultures in LB medium (5 g/l yeast extract; 10 g/l tryptone, 5 g/l sodium chloride) which cultures had an optical density of 0.1 as measured at 600 nm, were incubated with shaking at 37° C. with different concentrations of the P18 peptide. Bacterial growth was monitored by measuring the optical density after 24 h. Complete inhibition of growth (optical density at 600 nm after 24 h<0.15) was achieved at a peptide concentration from 31 ppm. It was possible to improve the antimicrobial activity further by amidating the C-terminal carboxyl group. For this, said carboxyl groups were activated with 1-ethyl-3-(3-dimethylaminopropyl)carbodiimide hydrochloride and N-hydroxy-sulfosuccinimide, and amidated by subsequent addition of ammonia.

Example 3

Production of Peptide Min (SEQ ID NO: 26)

A synthetic gene, AEMin$_4$ (SEQ ID NO:27), was cloned into the vector pAZL described in Hummerich et al. Biochemistry 43; 13604-13612 (2004), using the restriction endonucleases BamHI and HindIII, and dimerized according to the protocol described there, and cloned into the vector pET21 (Novagen). The sequence subsequently present in said vector codes for the repetitive precursor protein AEMin$_8$ (SEQ ID NO:28). Said repetitive precursor protein comprises 8 repeats, each of which comprises a copy of the Min peptide and an auxiliary sequence. The auxiliary sequence comprises a polyalanine sequence and imparts self-assembling properties to the repetitive precursor protein. The auxiliary sequence moreover comprises a negatively charged protective sequence. The amino acids Asp-Pro which are intended to enable the P18 peptide to be selectively cleaved out of the precursor protein using acids are located between the auxiliary sequences and the peptide sequences. The expression was carried out in the strain *E. coli* BL21 [DE3] (Novagen).

Cultivation and protein synthesis were carried out in a fed batch process at pO$_2$>20% and pH=6.8. Medium, trace salt solution and feeding solution had the composition described in example 1.

After the glycerol present in the basic medium had been exhausted, a constant feed at a rate of 100 ml/h was started.

Protein synthesis was induced by adding 1 mM isopropyl β-D-thiogalactopyranoside, after the bacterial culture had reached an optical density of $OD_{600}=60$. At this point, the temperature of the culture was lowered from 37° C. to 30° C. The cells were harvested 5 h after induction.

$AEMin_8$ was purified according to the following protocol:
Resuspension of the cell pellet in 5 ml of 20 mM MOPS (3-(N-morpholino)propanesulfonic acid) pH 7.0 per gram of wet mass
Disruption of the cells in a high pressure homogenizer at 1400 bar
Centrifugation, 30 min at 5000×g
Incubation of the supernatant, 20 min at 80° C.
Centrifugation, 30 min at 5000×g
Precipitation of $AEMin_8$ from the supernatant by adding 2 M ammonium sulfate (final concentration) at 4° C. overnight
Washing of the pellet with 8 M urea
2× washing of the pellet with water
Lyophilization
The lyophilized $AEMin_8$ was brought to −20° C.
From each liter of culture medium, 0.4 g of pure $AEMin_8$ were recovered.

For cleavage, 250 mg of the lyophilized $AEMin_8$ precursor protein were resuspended in 12.5 ml of 1% phosphoric acid and incubated at 90° C. for 8 h. After cooling to room temperature, insoluble substances were removed from the soluble components by sedimentation at 18000×g. The remaining solution was neutralized with 2 M NaOH. The solution was then lyophilized. The lyophilizate comprised the desired cleavage product and sodium hydrogen phosphate from neutralization of the phosphoric acid.

Figure 6:
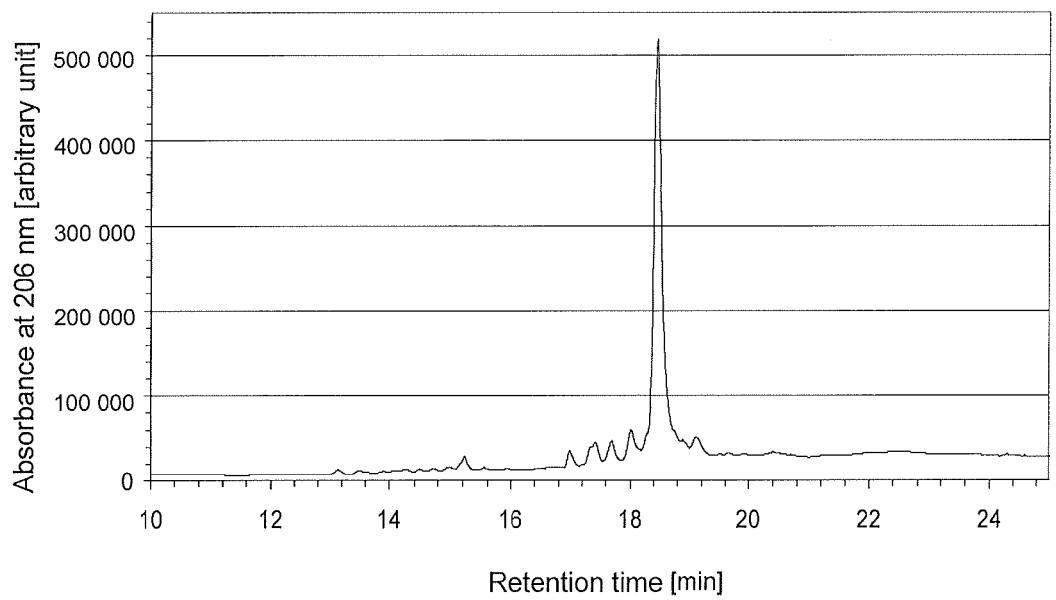
FIG. 6 depicts the reversed phase chromatogram of the peptide "Min" after acidic cleavage.
Figure 7:
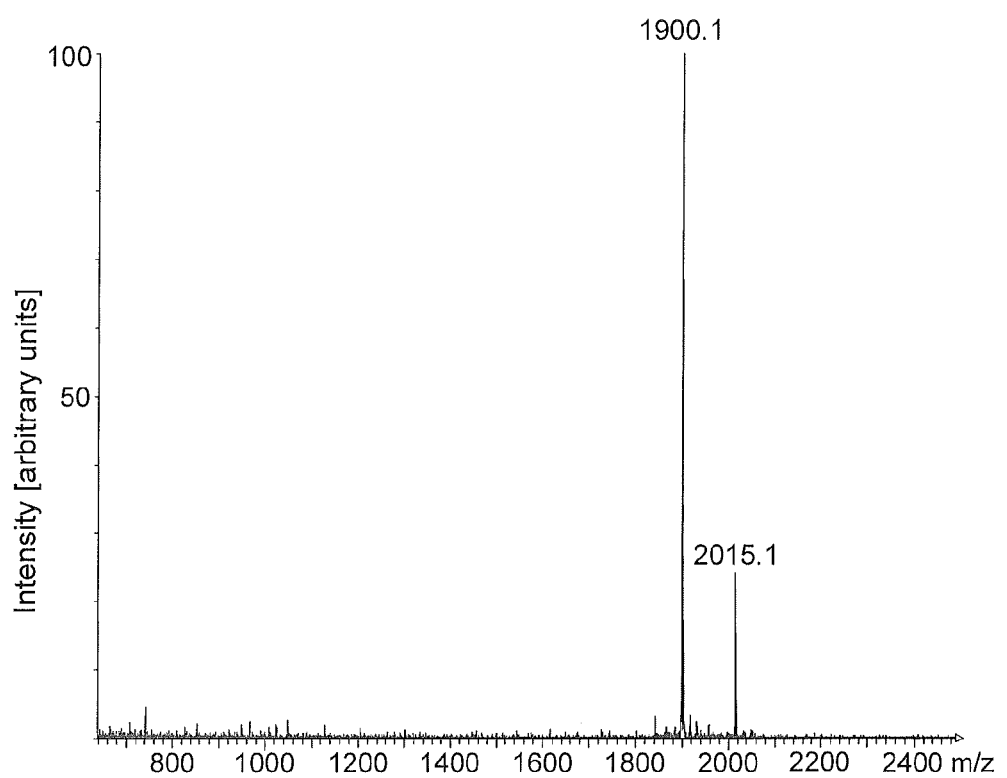
FIG. 7 depicts the mass spectrum of the "Min" peptide after acidic cleavage and reversed phase HPLC; the numbers shown indicate the m/z value of the particular monoisotopic peak.

The lyophilized product was analyzed by means of HPLC: for this, the product was dissolved at a concentration of 1 mg/ml in water and analyzed using a reversed phase chromatographic column (Jupiter Proteo 4.6×250 mm; Phenomenex). The eluent used was 0.1% trifluoroacetic acid in water, which was replaced with 0.1% trifluoroacetic acid in acetonitrole, using a linear gradient. Detection was carried out at 206 nm (FIG. 6). For further analysis, the fractions of the main peak were collected and the substance present therein was studied further. N-terminal sequencing confirmed that this component is the Min peptide. Studies by means of peptide mass spectrometry (MALDI-TOF) established a mass of 1900, which is identical to the theoretical mass of the Min peptide (FIG. 7). HPLC analysis revealed a purity of 68% based on UV-active components.

Example 4

Optimizing Production of Peptide P18 (SEQ ID NO: 23)

In order to increase the yield of peptide P18 from example 2, the influence of different Aux sequences on peptide yield was studied. Expression and overall yield were markedly increased using the synthetic gene $AHe2AP18_2$ (SEQ ID NO:74) which, after cloning into the pET21 vector according to example 2, codes for the precursor protein having SEQ ID NO:75. Fermentation was carried out under the conditions described in example 2.

The wet biomass was purified according to the following protocol:
Resuspension of the cell pellet: for each g of biomass, 6 g of water were added and mixed thoroughly.
Disruption of the cells in a high pressure homogenizer at 1500 bar
Addition of phosphoric acid to pH=3±0.5
10 min incubation at 23° C. with stirring
Centrifugation: 20 min, at least 5000×g
Resuspension of the pellet: for each g of wet mass add 20 ml of 0.4 M NaOH, homogenize and incubate with stirring at 23° C. for 1 hour
Neutralization: adjust pH of 8.5±0.5 with 1 M potassium phosphate buffer pH 6.0
Centrifugation: 20 min, at least 5000×g
The pellet consisting of washed inclusion bodies comprising the P18 precursor protein was hydrolyzed or cleaved by means of 2% strength $H_3PO_4$.
Cleavage Conditions:
i. use 7 ml of $H_3PO_4$ for each g of pellet
ii. homogenize
iii. incubate with shaking at 90° C. for 16 hours
Let cleavage reaction mixture cool down
Centrifugation: 20 min, at least 5000×g
Adjust pH of 4.0±0.5 with 25% NaOH
Centrifugation: 20 min, at least 5000×g
Dilute supernatant with water until conductivity less than 30 mS/cm
Purify P18 from supernatant via cation exchange chromatography (SP-Sepharose High Performance; GE Healthcare); washing buffer: 10 mM sodium acetate buffer pH 4+450 mM NaCl; elution buffer: 10 mM sodium acetate buffer pH 4+1100 mM NaCl
Precipitation of peptide by adding 25% NaOH to the eluate until pH=10.5±0.3
Centrifugation: 20 min, at least 5000×g
Resuspension of the pellet in 5 ml of water for each g of wet mass
Dissolving of the peptide: addition of acetic acid to pH 6.0 pH=10.5±0.5
Lyophilization
From each liter of fermentation culture, approx. 1 g of pure P18 peptide can be obtained in the manner described.

Example 5

Production of Peptide SEQ ID NO: 6

The peptides listed in examples 1 to 4 were derived from the repetitive precursor protein by acidic cleavage. This involves hydrolysis of the peptide bond between an aspartate and a proline. Accordingly, as shown in example 1, the peptide sequence starts N-terminally with a proline and ends C-terminally with an aspartate. Unter certain circumstances, the C-terminal aspartate, as shown in examples 2 and 3, may likewise be cleaved off, thereby allowing production of peptide sequences with a free-to-choose C-terminal sequence.

The peptide having SEQ ID NO:6 was produced in order to demonstrate that the method of the invention can also be used for producing peptides whose N terminus does not start with a proline but the first N-terminal amino acid of which can be chosen freely. For this, the precursor protein having SEQ ID NO:77 was produced using the synthetic gene $AHe2AP18_2$-P-G (SEQ ID NO:76), according to example 4. This precursor protein differs from the precursor protein SEQ ID NO:75 of example 4 only in that the N-terminal amino acids of the P18 peptide, Pro-Gly, and the C-terminal Gly have been deleted. Cloning and fermentation was carried out under the conditions described in example 4.

The wet biomass was purified according to the following protocol:
Resuspension of the cell pellet: for each g of biomass, 6 g of water were added and mixed thoroughly.

Disruption of the cells in a high pressure homogenizer at 1500 bar

Centrifugation: 20 min, at least 5000×g

The pellet consisting of inclusion bodies comprising the P18 precursor protein was hydrolyzed or cleaved by means of 5% strength $H_3PO_4$.

Cleavage Conditions:
  i. use 5 ml of $H_3PO_4$ for each g of pellet
  ii. homogenize
  iii. incubate with shaking at 90° C. for 16 hours Let cleavage reaction mixture cool down Centrifugation: 20 min, at least 5000×g Adjust pH of 4.0±0.5 with 25% NaOH Centrifugation: 20 min, at least 5000×g Dilute supernatant with water until conductivity less than 30 mS/cm Purify peptide from supernatant via cation exchange chromatography (SP-Sepharose High Performance; GE Healthcare); washing buffer: 10 mM sodium acetate buffer pH 4+450 mM NaCl; elution buffer: 10 mM sodium acetate buffer pH 4+1100 mM NaCl Precipitation of peptide by adding 25% NaOH to the eluate until pH=10.5±0.3

Centrifugation: 20 min, at least 5000×g

Resuspension of the pellet in 5 ml of water for each g of wet mass

Dissolving of the peptide by adding acetic acid until pH=6.0±0.5

Lyophilization

Figure 8:
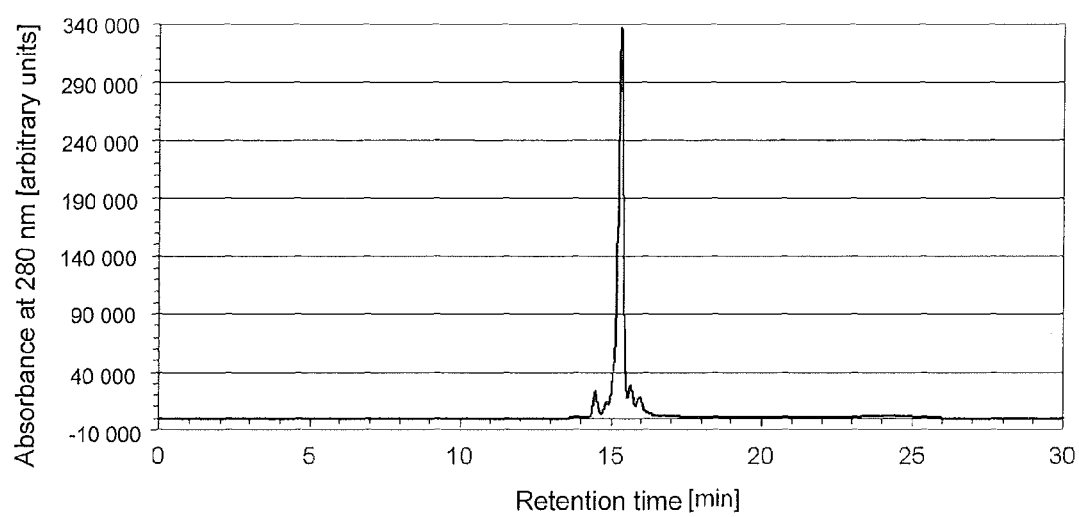
FIG. 8 depicts the reversed phase chromatogram of the peptide SEQ ID NO:6 after acidic cleavage and cation exchange chromatography.
Figure 9:
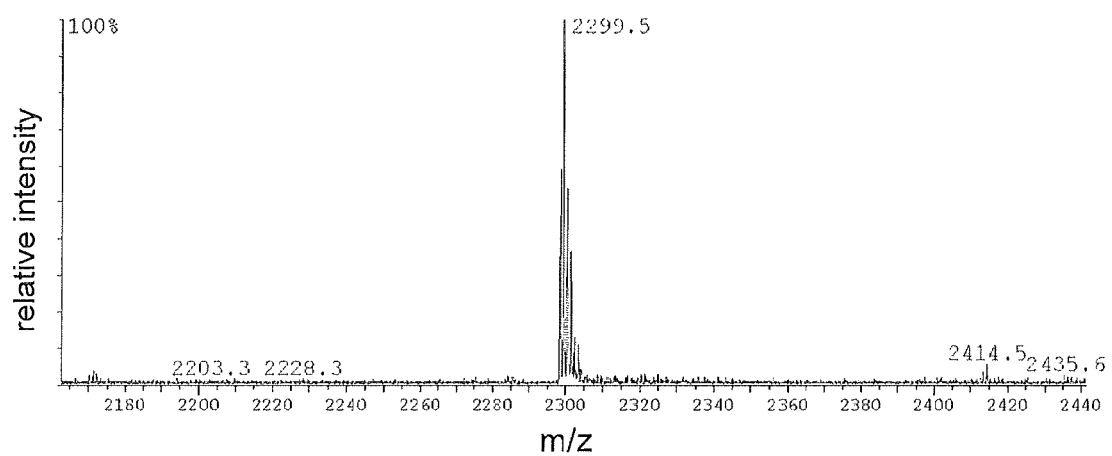
FIG. 9 depicts the mass spectrum of the SEQ ID NO:6 peptide after acidic cleavage, cation exchange chromatography and reversed phase HPLC; the numbers shown indicate the m/z value of the particular monoisotopic peak.

The lyophilized product was analyzed by means of HPLC. For this, the product was dissolved at a concentration of 1 mg/ml in water and analyzed using a reversed phase chromatographic column (Jupiter Proteo 4.6×250 mm; Phenomenex). The eluent used was 0.1% trifluoroacetic acid in water, which was replaced with 0.1% trifluoroacetic acid in acetonitrile, using a linear gradient. Detection was carried out at 280 nm (FIG. 8). For further analysis, the fractions of the main peak were collected and the substance present therein was studied further. Studies using mass spectrometry (MALDI-TOF) revealed a mass of 2300.6 for the peptide, which is equal to the theoretical mass of the SEQ ID NO:6 peptide (FIG. 9).

Example 6

Amidation of Lyophilized Peptide P18 (SEQ ID NO: 23)

In some cases, it may be advantageous to the activity of a peptide if the C terminus is amidated rather than being a free carboxyl group. To demonstrate this, lyophilized P18 peptide of example 4 was amidated according to the protocol below:

10 mg/ml P18 peptide
30% EtOH
10 mM 2-(N-morpholino)ethanesulfonic acid pH 5.0
3 M ammonium chloride
2.5 mM N-hydroxysuccinimide
50 mM 1-ethyl-3-(3-dimethylaminopropyl)carbodiimide
Incubation for 2 h at RT
Neutralization with NaOH pH 7.0

Figure 10:
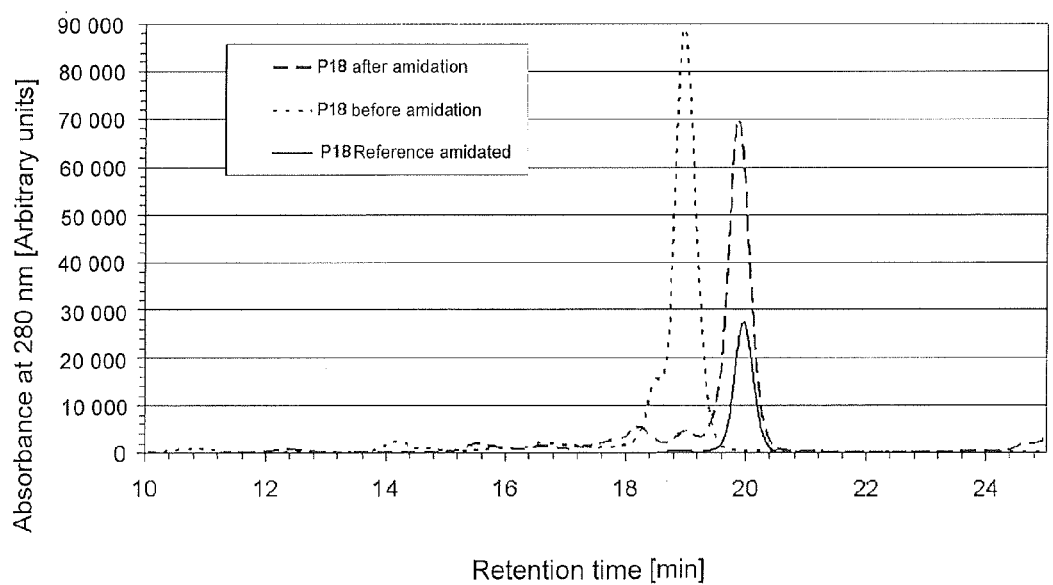
FIG. 10 depicts the HPLC cation exchange chromatogram of the "P18" peptide before and after amidation according to example 6; the chromatogram of a chemically synthesized and amidated reference peptide with the sequence of the "P18" peptide is shown for comparison.

The amidated sample was analyzed by HPLC using a Luna SCX 5µ 100 A chromatographic column (Phenomenex, Torrance, Calif., USA): the eluent used was 20 mM $KH_2PO_4$ pH 2.5 with 25% acetonitrile, which was replaced with 20 mM $KH_2PO_4$ pH 2.5; 25% acetonitrile and 1 M KCl, using a linear gradient. Detection was carried out at 280 nm (FIG. 10). FIG. 10 depicts, for comparison, the chromatogram of a chemically synthesized and amidated reference peptide with the sequence of the "P18" peptide (produced on order by Bachem A G, Bubendorf, Switzerland).

The peptide was purified further by cation exchange chromatography as described in example 4.

Example 7

Production of Peptide P18 (SEQ ID NO: 23) with Integrated Amidation

To improve cost efficiency of the production of amidated P18 peptide, amidation was integrated into the work-up procedure rather than carried out after a peptide purification, as described in example 6. For this, the precursor protein SEQ ID NO:75 was obtained by fermentation according to example 4, and the peptide was released from the precursor protein by acidic cleavage.

Subsequently, the following steps were carried out:

Let cleavage reaction mixture cool down

Centrifugation: 20 min, at least 5000×g

Adjust pH of 10.5±0.5 with 25% NaOH

Centrifugation: 20 min, at least 5000×g

Dissolve pellet in 3 ml of ethanol for each g of wet mass

Centrifuge; determination of peptide in the supernatant (diluting)

Mixing of the following components:
  a. 12.5 ml of dissolved peptide in ethanol
  b. 4.2 ml of water
  c. Addition of 400 µl of 500 mM 2-(N-morpholino)ethanesulfonic acid
  d. Adjust to pH 5.0 with HCl
  e. Addition of 2.14 g of ammonium chloride
  f. 200 µl of 500 mM N-hydroxysuccinimide
  g. 1 ml 1 MY of 1-ethyl-3-(3-dimethylaminopropyl)carbodiimide Incubation for 2 h at RT Dilute mixture with water until conductivity less than 30 mS/cm Purify modified P18 peptide via cation exchange chromatography (SP-Sepharose High Performance; GE Healthcare); washing buffer: 10 mM sodium acetate buffer pH 4+450 mM NaCl; elution buffer: 10 mM sodium acetate buffer pH 4+1100 mM NaCl Precipitation of peptide by adding 25% NaOH to the eluate until pH=10.5±0.3

Centrifugation: 20 min, at least 5000×g

Resuspension of the pellet in 5 ml of water for each gram of wet mass

Dissolving of the peptide: addition of acetic acid to pH 6.0±0.5

Lyophilization

Figure 11:
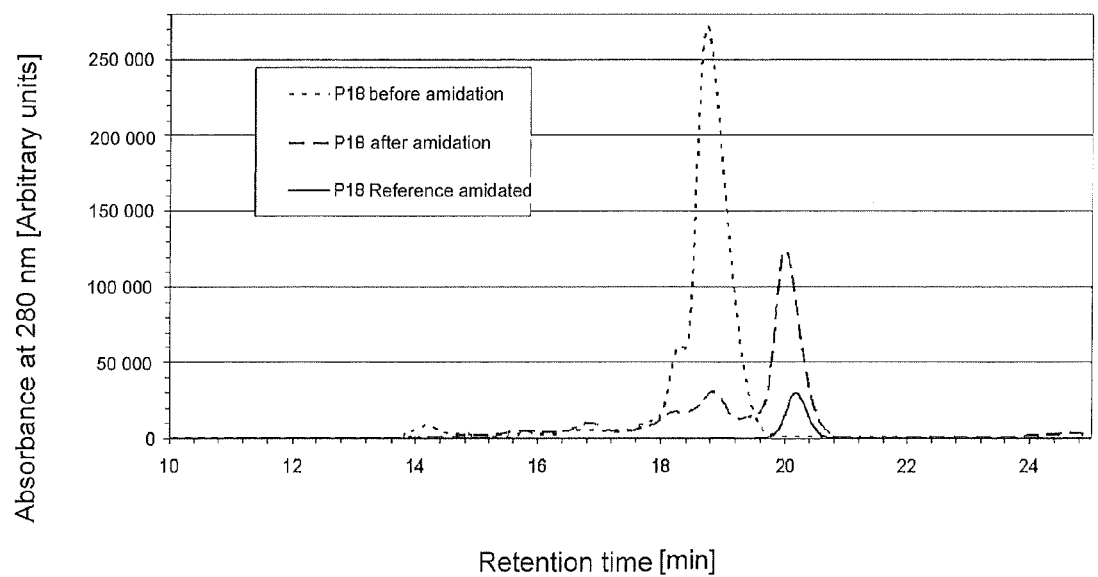
FIG. 11 depicts the HPLC cation exchange chromatogram of the "P18" peptide before and after amidation according to example 7; the chromatogram of a chemically synthesized and amidated reference peptide with the sequence of the "P18" peptide is shown for comparison.

The amidated sample was analyzed by HPLC using a Luna SCX 5µ 100 A chromatographic column (Phenomenex, Torrance, Calif., USA). The eluent used was 20 mM $KH_2PO_4$ pH 2.5 with 25% acetonitrile, which was replaced with 20 mM $KH_2PO_4$ pH 2.5; 25% acetonitrile and 1 M KCl, using a linear gradient. Detection was carried out at 280 nm (FIG. 11). FIG. 11 depicts, for comparison, the chromatogram of a chemically synthesized and amidated reference peptide with the sequence of the "P18" peptide (produced on order by Bachem A G, Bubendorf, Switzerland).

Overview of Sequences According to the Invention

| SEQ ID NO: | Sequence | Name Type |
| --- | --- | --- |
| 1 | GSSAAAAAAAASGP | SA |
| 2 | GSSAAAAAAAAASGP | SA |
| 3 | GSAAAAAAAASGP | SA |
| 4 | GSVVVVVVVSGP | SA |
| 5 | GSVVAAVVAASGP | SA |
| 6 | KWKLFKKIPKFLHLAKKF | Pep |
| 7 | $X_1$ $X_2$K $X_3$ $X_4$ $X_5$KIP $X_{10}$ KF$X_6X_7$ $X_8$ A$X_9$KF | Pep |
| 8 | $X_1$ $X_2$K $X_3$ $X_4$ $X_5$KIP $X_{11}$ $X_{12}$ KF$X_6X_7$ $X_8$ A$X_9$KF | Pep |
| 9 | KWKLFKKIPPKFLHLAKKF | Pep |
| 10 | RWKLFKKIPKFLHLAKKF | Pep |
| 11 | FKKLFKKIPKFLHAAKKF | Pep |
| 12 | KWKLLKKIPKFKKLALKF | Pep |
| 13 | KWKLFKKIPKFLHAAKKF | Pep |
| 14 | KWKKFLKIPKFLHAAKKF | Pep |
| 15 | KWKKLLKIPKFLHAAKKF | Pep |
| 16 | FEEISEFLQSLEEF | SU helical |
| 17 | EWELFEEISEFLQSLEEF | SU helical |
| 18 | ELFEELAEFLQQLEEFIE | SU helical |
| 19 | LFEELQEFLQALEELAQFALQFLAAFLQFS | SU helical |
| 20 | PEAHVMHKVAPRPGGGSCGD | Pep (ZnO) |
| 21 | GGATCCATGGGTTCCAGCGCTGCGGCAGCTGCAGCGGCTG CAAGTGGTCCGGACCCGGAGGCACACGTTATGCACAATAGC GCCGCGTCCGGGTGGCGGTTCTTGTGGTGATCCGGGTAGC TCTGCGGCTGCAGCTGCGGCTGCAGCTTCCGGTCCGGACC CGGAAGCTCACGTTATGCACAAGGTTGCTCCACGCCCG GGCGGTGGCAGCTGCGGTGATCCAGCAGCTCTGCTGCG GCTGCGGCAGCGGCCGCTTCTGGCCCGGACCCGGAAGCT CACGTTATGCACAAAGTGGCTCCGCGTCCGGGTGGCGG TTCCTGCGGGATCCGGGTTCTT-CCGCTGCAGCGGCTGCGGCCGCAGCGTCTGGCCCGGAC CCGAAGCA CATGTTATGCATAAAGTAGCGCCGCGTCCGGGCGGTGGCTC TTGCGGTGACCCGGGCTAATGAAAGCTT | ZnO4 construct |
| 22 | MASMTGGQQMGRGSM GSSAAAAAAAASGPD PEAHVMHKVAPRPGGGSCGDPGSSAAAAAAAASGPDPEAH-VMHKVAPRPGGGSCGDPGSSAAAAAAAASGPDPEAHVMHKVA-PRPGGGSCGDPGSSAAAAAAAASGPDPEAHVMHKVA-PRPGGGSCGDPGSSAAAAAAAASGPDPEAHVMHKVA-PRPGGGSCGDPGSSAAAAAAAASGPDPEAHVMHKVA-PRPGGGSCGDPGSSAAAAAAAASGPDPEAHVMHKVA-PRPGGGSCGDPG | ZnO8 precursor peptide |
| 23 | PGKWKLFKKIPKFLHLAKKFG | Pep (P18) |
| 24 | GGATCCATGGGCTCTAGCGCTGCAGCGGCAGCTGCCGCGGCT TCTGGTCCGGGTCTGTTCGAAGAGATCTCCGAATTCCTGCA GTCTCTGGAAGAGTTCGGTGGCCCGGGTTCCTCTGCAGCTG CGGCTGCAGCTGCGGCAAGCGGCCCTGACCCAGGTAAATGGA AACTGTTTAAGAAAATTCCGAAATTCCTGCATCTGGCTAAAAAT TCGGTGACCCGGGTTCTTCCGCTGCGGCTGCAGCTGCAGCT GCGTCCGGTCCGGGTCTGTTCGAAGAAATCTCCGAATTCCTGC AGTCTCTGGAAGAATTCGGCGGTCCGGGCTCTAGCGCTGCCGC TGCAGCGGCAGCGGCTTCCGGCCCGGACCCGGGCAAATGGA AACTGTTTAAGAAAATCCCGAAATTTCTGCATCTGGCTAAAAAGT TCGGCGATCCGGGCTAATGAAAGCTT | AheAP18₂ construct |

| SEQ ID NO: | Sequence | Name Type |
|---|---|---|
| 25 | MASMTGGQQMGRGSM<br>GSSAAAAAAAASGPGLFEEISEFLQSLEEFGGPGSSAAAAAAAAS-<br>GPD<br>PGKWKLFKKIPKFLHLAKKFGDP<br>GSSAAAAAAAASGPGLFEEISEFLQSLEEFGGPGSSAAAAAAAASGPD<br>PGKWKLFKKIPKFLHLAKKFGDP<br>GSSAAAAAAAASGPGLFEEISEFLQSLEEFGGPGSSAAAAAAAASGPD<br>PGKWKLFKKIPKFLHLAKKFGDP<br>GSSAAAAAAAASGPGLFEEISEFLQSLEEFGGPGSSAAAAAAAASGPD<br>PGKWKLFKKIPKFLHLAKKFGDPG | AheAP18$_4$<br>precursor<br>peptide |
| 26 | PGERKRLIGCSVMTKPAG | Pep (Min) |
| 27 | GGATCCATGGGCTCTTCCGCTGCAGCCGCTG-<br>CAGCTGCGGCTGCATCCGGTCCGGAGGCAGAGCCGGAA-<br>GACCCGGGTGAACGT<br>AAACGTCTGATCGGTTGTTCTGTAATGACCAAACCTGCTGGT<br>GATCCGGGCTCCAGCGCTGCGGCTGCGGCAGCTGCAGCGGCC<br>TCTGGTCCGGAGGCGGAACCGGAGGACCCGGGTGAACGTAAG<br>CGCCTGATCGGCTGCAGCGTGATGACCAAACCGGCTGGTGAT<br>CCGGGTTCTTCCGCGGCTGCAGCTGCGGCAGCTGCAGCTAGTG<br>GTCCAGAAGCAGAACCAGAAGACCCGGGTGAACGTAAACGTCT<br>GATTGGTTGCTCTGTTATGACTAAACCGGCTGGTGACCCGGGC<br>TCTTCCGCGGCTGCCGCGGCTGCGGCTGCAGCTAGCGGCCCG<br>GAAGCTGAACCGGAAGATCCGGGCGAACGCAAGCGTCTGATCG<br>GCTGCTCCGTTATGACTAAAC-<br>CGGCTGGCGACCCGGGCTAATGAAAGCTT | AEMin$_4$<br>construct |
| 28 | MASMTGGQQMGRGSM<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDP<br>GSSAAAAAAAASGPEAEPEDPGERKRLIGCSVMTKPAGDPG | AEMin$_8$<br>precursor<br>peptide |
| 29 | NPSSLFRYLPSD | Pep |
| 30 | HGGGHGHGGGHG | Pep |
| 31 | HYPTLPLGSSTY | Pep |
| 32 | ALSPHSAPLTLY | Pep |
| 33 | SAGRLSA | Pep |
| 34 | TLPNHTV | Pep |
| 35 | HTSKLGI | Pep |
| 36 | MSPHPHPRHHHTGGGK | Pep |
| 37 | EAHVMHKVAPRPGGGSC | Pep<br>(ZnO short) |
| 38 | SSKKSGSYSGSKGSRRIL | Pep |
| 39 | PYAYMKSRDIESAQSDEEVELRDALAD | Pep |
| 40 | PGYGYYKNRNAEPAAAEAVD | Pep |
| 41 | PGKSRDIESAQSDEEVELRD | Pep |
| 42 | PGKSRDAEPAAAGEEVD | Pep |
| 43 | SSKKSGSYSGSKGSRRILGGGNPSSLFRYLPSD | Pep |
| 44 | MSPHPHPRHHHTGGGNPSSLFRYLPSD | Pep |
| 45 | NPSSLFRYLPSDGGGRREEWWDDRREEWWDD | Pep |
| 46 | MSPHPHPRHHHTGGGHGGGHGHGGGHG | Pep |
| 47 | SSKKSGSYSGSKGSRRILGGGHGGGHGHGGGHG | Pep |

-continued

| SEQ ID NO: | Sequence | Name Type |
|---|---|---|
| 48 | SSKKSGSYSGSKGSRRILGGGHYPTLPLGSSTY | Pep |
| 49 | SSKKSGSYSGSKGSRRILGGGSAGRLSA | Pep |
| 50 | RREEWWDDRREEWWDD | Pep |
| 51 | MKQLADSLMQLARQVSRLESA | Pep |
| 52 | MKQLADSLHQLARQVSRLEHA | Pep |
| 53 | LMQLARQMKQLADSLMQLARQVSRLESA | Pep |
| 54 | MKELADSLMQLARQVDRLESA | Pep |
| 55 | MKQLADSLHQLAHQVSHLEHA | Pep |
| 56 | PHFRFSFSP | Pep |
| 57 | PHFSFSFSP | Pep |
| 58 | PSFRFSFSP | Pep |
| 59 | MEELADSLEELARQVEELESA | Pep |
| 60 | MKKLADSLKKLARQVKKLESA | Pep |
| 61 | PHFHFSFSP | Pep |
| 62 | PHFSFHFSP | Pep |
| 63 | MKQLADSLHQLAHKVSHLEHA | Pep |
| 64 | EISALEKEISALEKEISALEK | Pep |
| 65 | KISALKEKISALKEKISALKE | Pep |
| 66 | RADARADARA DARADA | Pep |
| 67 | VKVKVKVKVG PPTKVKVKVK V | Pep |
| 68 | EAEPED | SU non-helical |
| 69 | PGKWKLFKKIPKFLHLAKKFGD | Pep |
| 70 | PGERKRLIGCSVMTKPAGD | Pep |
| 71 | PGKWKLFKKIPKFLHLAKKFGN | Pep |
| 72 | ERKRLIGCSVMTKPA | Pep (Min short) |
| 73 | GAAAAAAAASGP | SA |
| 74 | GGATCCATGGGCGCTGCAGCGGCAGCTGCCGCGGCTTCTGGTCCGGGTGAGTGGGAGCTGTTCGAAGAGATCAGCGMTTCCTGCAGTCTCTGGAAGAGTTCGGTGGCCCGGGTTCCTCTGCTGCTGCGGCTGCAGCTGCGGCAGGCCCGGGCGACCCAGGTAAATGGAAACTGTTTAAGAAAATTCCGAAATTCCTGCATCTGGCTAAAAAATTCGGTGACCCGGGTTCCTCTGCTGCGGCTGCAGCTGCAGCTGGTCCGGTCCGGGTGAATGGGAACTGTTCGAAGAAATCTCCGAATTCCTGCAGTCTCTGGAAGAATTCGGCGGTCCGGGCGCTGCCGCTGCAGCGGCAGCGGCTGGTCCTGCGACCCGGGCAAATGGAAACTGTTTAAGAAAATCCCGAAATTTCTGCATCTGGCTAAAAAGTTCGGCGATCCGGGCTAATGAAAGCTT | AHe2AP18$_2$ construct |
| 75 | MASMTGGQQMGRSMGAAAAAAAASGPGEWELFEEISEFLQSLEEFGGPGSSAAAAAAAAGPGDPGKWKLFKKIPKFLHLAKKFGDPGSSAAAAAAAAGSPGEWELFEEISEFLQSLEEFGGPGAAAAAAAGPGDPGKWKLFKKIPKFLHLAKKFGDPGAAAAAAAASGPGEWELFEEISEFLQSLEEFGGPGSSAAAAAAAAGPGDPGKWKLFKKIPKFLHLAKKFGDPGSSAAAAAAAAGSPGEWELFEEISEFLQSLEEFGGPGAAAAAAAAGPGDPGKWKLFKKIPKFLHLAKKFGDPG | AHe2AP18$_4$ precursor peptide |

| SEQ ID NO: | Sequence | Name Type |
|---|---|---|
| 76 | GGATCCATGGGCGCTGCAGCGGCAGCTGCCGCGGCTTCTGGT<br>CCGGGTGAGTGGGAGCTGTTCGAAGAGATCAGCGAATTCCTGC<br>AGTCTCTGGAAGAGTTCGGTGGCCCGGGTTCCTCTGCTGCTGC<br>GGCTGCAGCTGCGGCAGGCCCAGGCGACAAATGGAAACTGTTT<br>AAGAAAATTCCGAAATTCCTGCATCTGGCTAAAAAATTCGACCC<br>GGGTTCCTCTGCTGCGGCTGCAGCTGCAGCTGCGTCCGGTCCG<br>GGTGAATGGGAACTGTTCGAAGAAATCTCCGAATTCCTGCAGTC<br>TCTGGAAGAATTCGGCGGTCCGGGCGCTGCCGCTGCAGCGGC<br>AGCGGCTGGTCCTGGCGACAAATGGAAACTGTTTAAGAAAATCC<br>CGAAATTTCTGCATCTGGCTAAAAAGTTCGATCCGGGCTAATGA<br>AAGCTT | AHe2AP18-P-<br>G₂ construct |
| 77 | MGAAAAAAAASGPGEWELFEEISEFLQSLEEFGGPGSSAAAAAAA<br>AGPGDKWKLFKKIPKFLHLAKKFDPGSSAAAAAAAASGPGEWELF<br>EEISEFLQSLEEFGGPGAAAAAAAAGPGDKWKLFKKIPKFLHLAKK<br>FDPGAAAAAAAASGPGEWELFEEISEFLQSLEEFGGPGSSAAAAA<br>AAAGPGDKWKLFKKIPKFLHLAKKFDPGSSAAAAAAAASGPGEWE<br>LFEEISEFLQSLEEFGGPGAAAAAAAAGPGDKWKLFKKIPKFLHLAK<br>KFDPG | AHe2AP18-P-<br>G₄<br>precursor<br>peptide |

SA = self-assembling sequence
SU = protective peptide
Pep = peptide to be produced In addition to the above-described specific Pep amino acid sequences, the sequences listed may be altered to C-terminally and/or N-terminally due to the addition of specific cleavage sequences (e.g. between the residues "DP" for an acidic cleavage; or between the residues "NG" for a hydroxylamine cleavage) or due to the remaining amino acid residues resulting from such cleavages. Optionally, a spacer residue such as, for example, a G residue may also additionally be inserted between cleavage sequence and Pep sequences. Particular mention should be made of the following alterations to the above Pep sequences, which can result from acidic or hydroxylamine cleavage of Pep sequences produced according to the invention:
N-terminally: addition of a PG-, P- or G-residue;
C-terminally: addition of a GD-; GN-; G-; N- or D-residue
Such alterations apply in particular to every single one of the above Pep sequences, in particular those of SEQ ID NO:6 to 15, 29 to 67 and 72.

Reference is explicitly made to the disclosure of the literature cited herein.

The invention claimed is:

1. A synthetic precursor protein comprising a cleavable repetitive sequence of desired peptide (Pep) elements and auxiliary peptide (Aux) elements of the general formula (Pep-Aux)$_x$ or (Aux-Pep)$_x$, where x>1, wherein the Aux elements are identical or different and comprise amino acid sequence elements which impart to said precursor protein self-assembling properties, wherein at least one Aux element comprises a self-assembling peptide ((SA) element), wherein the SA element comprises at least one of the following sequence motifs:
A$_n$ (motif 1)
(GA)$_m$ (motif 2)
V$_n$ (motif 3)
(VA)$_m$ (motif 4)
(VVAA)$_o$ (motif 5)
wherein A is alanine, G is glycine, V is valine, n is an integer from 5 to 12, m is an integer from 4 to 10, and o is an integer from 2 to 6; and the Pep elements are identical or different and comprise the amino acid sequence of identical or different peptide molecules having a sequence length of 5 to 70 amino acid residues, and the Pep elements are flanked by cleavage sequences which enable the Pep elements to be specifically cleaved out of the precursor protein, wherein the elements Pep and Aux are peptidically linked to one another and the peptidic linkage is specifically cleavable chemically or enzymatically, wherein the Pep element comprises a cationic antimicrobial peptide sequence, and wherein optionally at least one Aux peptide additionally comprises a protective peptide (SU) element, said SU element having an increased proportion of negatively charged amino acid residues, such that the overall net charge of the precursor protein at pH=7 is greater than −10 and less than +10.

2. The synthetic precursor protein according to claim 1, wherein said precursor protein forms stable associates by itself during expression, and wherein said stable associates cannot be dissolved at room temperature by 0.2 M NaOH in one hour or by 2 M urea or 1 M guanidinium hydrochloride in 10 min.

3. The synthetic precursor protein according to claim 1, wherein the SA element comprises an amino acid sequence selected from the group consisting of SEQ ID NO: 1 to SEQ ID NO: 5 and SEQ ID NO: 73.

4. The precursor protein according to claim 1, wherein the SU element in the precursor protein is capable of forming an amphiphilic helical structure.

5. The precursor protein according to claim 4, wherein the SU element is an amphiphilic peptide comprising a sequence segment of at least seven peptidically linked amino acids capable of forming an amphiphilic alpha-helix, wherein the amino acid residues of said helix in its vertical projection are separated into a hydrophobic half and a hydrophilic half of the helix, the hydrophobic half of the helix having at least 3 adjacent in the vertical projection identical or different hydrophobic amino acid residues, and the hydrophilic half of the helix having at least 3 adjacent in the vertical projection identical or different hydrophilic amino acid residues.

6. The precursor protein according to claim 1, wherein the SU element comprises an amino acid sequence selected from the group consisting of SEQ ID NO: 16 to SEQ ID NO: 19 and SEQ ID NO: 68.

7. The precursor protein according to claim 1, wherein the Pep element comprises an amino acid sequence selected from the group consisting of SEQ ID NO: 6 to SEQ ID NO: 15, SEQ ID NO: 23, SEQ ID NO: 26 and SEQ ID NO: 69 to SEQ ID NO: 72.

8. The precursor protein according to claim 1, wherein the Pep element comprises an amino acid sequence selected from the group consisting of SEQ ID NO: 20 or SEQ ID NO: 29 to 67.

9. The precursor protein according to claim 1, wherein the Aux elements independently of one another have any of the following meanings:
SA,
SA-SU,
SU-SA,
SA-SU-SA,
SU-SA-SU,
wherein the elements SA and SU are peptidically linked to one another, and the Aux elements are peptidically linked terminally to at least one Pep element, and this peptidic linkage to the Pep elements is specifically cleavable chemically or enzymatically.

10. A nucleic acid sequence coding for the synthetic precursor protein according to claim 1.

11. The nucleic acid sequence according to claim 10, selected from the group consisting of SEQ ID NO: 21, 24, 27, 74, and 76.

12. An expression cassette comprising at least one nucleic acid sequence according to claim 10, operatively linked to at least one regulatory nucleic acid sequence.

13. A recombinant vector for transforming a eukaryotic or prokaryotic host, comprising the nucleic acid sequence according to claim 10, or an expression cassette comprising at least one of said nucleic acid sequence operatively linked to at least one regulatory nucleic acid sequence.

14. A method of producing a desired peptide (Pep), which comprises:
a) producing a precursor protein according to claim 1; and
b) removing the Pep peptides from the precursor protein.

15. The method according to claim 14, wherein the precursor protein is produced in a recombinant microorganism comprising at least one vector comprising:
a) a nucleic acid sequence encoding said precursor protein; or
b) an expression cassette comprising at least one of said nucleic acid sequence operatively linked to at least one regulatory sequence.

16. The method according to claim 15, wherein the precursor protein is produced in a recombinant *E. coli* strain.

17. The method according to claim 14, wherein the expressed precursor protein, optionally after having been converted into a stably associated form, is purified and cleaved chemically or enzymatically to release the desired peptide (Pep).

* * * * *

SEQUENCE LISTING

```
<160> NUMBER OF SEQ ID NOS: 77

<210> SEQ ID NO 1
<211> LENGTH: 14
<212> TYPE: PRT
<213> ORGANISM: Artificial Sequence
<220> FEATURE:
<223> OTHER INFORMATION: Polypeptide

<400> SEQUENCE: 1

Gly Ser Ser Ala Ala Ala Ala Ala Ala Ala Ala Ser Gly Pro
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Polypeptide

<400> SEQUENCE: 2

Gly Ser Ser Ala Ala Ala Ala Ala Ala Ala Ala Ser Gly Pro
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Polypeptide
```

-continued

<400> SEQUENCE: 3

Gly Ser Ala Ala Ala Ala Ala Ala Ala Ser Gly Pro
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Polypeptide

<400> SEQUENCE: 4

Gly Ser Val Val Val Val Val Val Val Ser Gly Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Polypeptide

<400> SEQUENCE: 5

Gly Ser Val Val Ala Ala Val Val Ala Ala Ser Gly Pro
1               5                   10

<210> SEQ ID NO 6
<211> LENGTH: 18
<212> TYPE: PRT
<213> ORGANISM: Artificial Sequence
<220> FEATURE:
<223> OTHER INFORMATION: P18 Peptide

<400> SEQUENCE: 6

Lys Trp Lys Leu Phe Lys Lys Ile Pro Lys Phe Leu His Leu Ala Lys
1               5                   10                  15

Lys Phe

<210> SEQ ID NO 7
<211> LENGTH: 19
<212> TYPE: PRT
<213> ORGANISM: Artificial Sequence
<220> FEATURE:
<223> OTHER INFORMATION: Sequence Motif 1
<220> FEATURE:
<221> NAME/KEY: MISC_FEATURE
<222> LOCATION: (1)..(1)
<223> OTHER INFORMATION: Xaa is a basic amino acid or hydrophobic amino
      acid different from Pro
<220> FEATURE:
<221> NAME/KEY: MISC_FEATURE
<222> LOCATION: (2)..(2)
<223> OTHER INFORMATION: Xaa is a basic amino acid or hydrophobic amino
      acid different from Pro
<220> FEATURE:
<221> NAME/KEY: MISC_FEATURE
<222> LOCATION: (4)..(4)
<223> OTHER INFORMATION: Xaa is a basic amino acid or hydrophobic amino
      acid different from Pro
<220> FEATURE:
<221> NAME/KEY: MISC_FEATURE
<222> LOCATION: (5)..(5)
<223> OTHER INFORMATION: Xaa is a basic amino acid or hydrophobic amino
      acid different from Pro
<220> FEATURE:
<221> NAME/KEY: MISC_FEATURE
<222> LOCATION: (6)..(6)
<223> OTHER INFORMATION: Xaa is a basic amino acid or hydrophobic amino
      acid different from Pro -continued

```
<220> FEATURE:
<221> NAME/KEY: MISC_FEATURE
<222> LOCATION: (10)..(10)
<223> OTHER INFORMATION: Xaa is a missing or is Pro or Pro-Pro
<220> FEATURE:
<221> NAME/KEY: MISC_FEATURE
<222> LOCATION: (13)..(13)
<223> OTHER INFORMATION: Xaa is a basic amino acid or hydrophobic amino
      acid different from Pro
<220> FEATURE:
<221> NAME/KEY: MISC_FEATURE
<222> LOCATION: (14)..(14)
<223> OTHER INFORMATION: Xaa is a basic amino acid or hydrophobic amino
      acid different from Pro
<220> FEATURE:
<221> NAME/KEY: MISC_FEATURE
<222> LOCATION: (15)..(15)
<223> OTHER INFORMATION: Xaa is a basic amino acid or hydrophobic amino
      acid different from Pro
<220> FEATURE:
<221> NAME/KEY: MISC_FEATURE
<222> LOCATION: (17)..(17)
<223> OTHER INFORMATION: Xaa is a basic amino acid or hydrophobic amino
      acid different from Pro

<400> SEQUENCE: 7

Xaa Xaa Lys Xaa Xaa Xaa Lys Ile Pro Xaa Lys Phe Xaa Xaa Xaa Ala
1               5                   10                  15

Xaa Lys Phe

<210> SEQ ID NO 8
<211> LENGTH: 20
<212> TYPE: PRT
<213> ORGANISM: Artificial Sequence
<220> FEATURE:
<223> OTHER INFORMATION: Sequence Motif 2
<220> FEATURE:
<221> NAME/KEY: MISC_FEATURE
<222> LOCATION: (1)..(1)
<223> OTHER INFORMATION: Xaa is Lys, Arg or Phe
<220> FEATURE:
<221> NAME/KEY: MISC_FEATURE
<222> LOCATION: (2)..(2)
<223> OTHER INFORMATION: Xaa is Lys or Trp
<220> FEATURE:
<221> NAME/KEY: MISC_FEATURE
<222> LOCATION: (4)..(4)
<223> OTHER INFORMATION: Xaa is Leu or Lys
<220> FEATURE:
<221> NAME/KEY: MISC_FEATURE
<222> LOCATION: (5)..(5)
<223> OTHER INFORMATION: Xaa is Phe or Leu
<220> FEATURE:
<221> NAME/KEY: MISC_FEATURE
<222> LOCATION: (6)..(6)
<223> OTHER INFORMATION: Xaa is Leu or Lys
<220> FEATURE:
<221> NAME/KEY: MISC_FEATURE
<222> LOCATION: (10)..(10)
<223> OTHER INFORMATION: Xaa is Pro or missing
<220> FEATURE:
<221> NAME/KEY: MISC_FEATURE
<222> LOCATION: (11)..(11)
<223> OTHER INFORMATION: Xaa is Pro or missing
<220> FEATURE:
<221> NAME/KEY: MISC_FEATURE
<222> LOCATION: (14)..(14)
<223> OTHER INFORMATION: Xaa is Leu or Lys
<220> FEATURE:
<221> NAME/KEY: MISC_FEATURE
<222> LOCATION: (15)..(15)
<223> OTHER INFORMATION: Xaa is His or Lys
<220> FEATURE:
<221> NAME/KEY: MISC_FEATURE
<222> LOCATION: (16)..(16)
<223> OTHER INFORMATION: Xaa is Ala, Leu, Val or Ser
```

```
<220> FEATURE:
<221> NAME/KEY: MISC_FEATURE
<222> LOCATION: (18)..(18)
<223> OTHER INFORMATION: Xaa is Leu or Lys

<400> SEQUENCE: 8

Xaa Xaa Lys Xaa Xaa Xaa Lys Ile Pro Xaa Xaa Lys Phe Xaa Xaa Xaa
1               5                   10                  15

Ala Xaa Lys Phe
            20

<210> SEQ ID NO 9
<211> LENGTH: 19
<212> TYPE: PRT
<213> ORGANISM: Artificial Sequence
<220> FEATURE:
<223> OTHER INFORMATION: Polypeptide

<400> SEQUENCE: 9

Lys Trp Lys Leu Phe Lys Lys Ile Pro Pro Lys Phe Leu His Leu Ala
1               5                   10                  15

Lys Lys Phe

<210> SEQ ID NO 10
<211> LENGTH: 18
<212> TYPE: PRT
<213> ORGANISM: Artificial Sequence
<220> FEATURE:
<223> OTHER INFORMATION: RP18 Peptide

<400> SEQUENCE: 10

Arg Trp Lys Leu Phe Lys Lys Ile Pro Lys Phe Leu His Leu Ala Lys
1               5                   10                  15

Lys Phe

<210> SEQ ID NO 11
<211> LENGTH: 18
<212> TYPE: PRT
<213> ORGANISM: Artificial Sequence
<220> FEATURE:
<223> OTHER INFORMATION: KKFP18 Peptide

<400> SEQUENCE: 11

Phe Lys Lys Leu Phe Lys Lys Ile Pro Lys Phe Leu His Ala Ala Lys
1               5                   10                  15

Lys Phe

<210> SEQ ID NO 12
<211> LENGTH: 18
<212> TYPE: PRT
<213> ORGANISM: Artificial Sequence
<220> FEATURE:
<223> OTHER INFORMATION: KKLP18 Peptide

<400> SEQUENCE: 12

Lys Trp Lys Leu Leu Lys Lys Ile Pro Lys Phe Lys Lys Leu Ala Leu
1               5                   10                  15

Lys Phe

<210> SEQ ID NO 13
<211> LENGTH: 18
<212> TYPE: PRT
<213> ORGANISM: Artificial Sequence
<220> FEATURE:
```

<223> OTHER INFORMATION: AP18 Peptide

<400> SEQUENCE: 13

Lys Trp Lys Leu Phe Lys Lys Ile Pro Lys Phe Leu His Ala Ala Lys
1               5                   10                  15

Lys Phe

<210> SEQ ID NO 14
<211> LENGTH: 18
<212> TYPE: PRT
<213> ORGANISM: Artificial Sequence
<220> FEATURE:
<223> OTHER INFORMATION: KFLP18 Peptide

<400> SEQUENCE: 14

Lys Trp Lys Lys Phe Leu Lys Ile Pro Lys Phe Leu His Ala Ala Lys
1               5                   10                  15

Lys Phe

<210> SEQ ID NO 15
<211> LENGTH: 18
<212> TYPE: PRT
<213> ORGANISM: Artificial Sequence
<220> FEATURE:
<223> OTHER INFORMATION: KLLP18 Peptide

<400> SEQUENCE: 15

Lys Trp Lys Lys Leu Leu Lys Ile Pro Lys Phe Leu His Ala Ala Lys
1               5                   10                  15

Lys Phe

<210> SEQ ID NO 16
<211> LENGTH: 14
<212> TYPE: PRT
<213> ORGANISM: Artificial Sequence
<220> FEATURE:
<223> OTHER INFORMATION: Polypeptide

<400> SEQUENCE: 16

Phe Glu Glu Ile Ser Glu Phe Leu Gln Ser Leu Glu Glu Phe
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Polypeptide

<400> SEQUENCE: 17

Glu Trp Glu Leu Phe Glu Glu Ile Ser Glu Phe Leu Gln Ser Leu Glu
1               5                   10                  15

Glu Phe

<210> SEQ ID NO 18
<211> LENGTH: 18
<212> TYPE: PRT
<213> ORGANISM: Artificial Sequence
<220> FEATURE:
<223> OTHER INFORMATION: Polypeptide

<400> SEQUENCE: 18

Glu Leu Phe Glu Glu Leu Ala Glu Phe Leu Gln Gln Leu Glu Glu Phe
1               5                   10                  15

Ile Glu

<210> SEQ ID NO 19
<211> LENGTH: 30
<212> TYPE: PRT
<213> ORGANISM: Artificial Sequence
<220> FEATURE:
<223> OTHER INFORMATION: Polypeptide

<400> SEQUENCE: 19

Leu Phe Glu Glu Leu Gln Glu Phe Leu Gln Ala Leu Glu Glu Leu Ala
1               5                   10                  15

Gln Phe Ala Leu Gln Phe Leu Ala Ala Phe Leu Gln Phe Ser
            20                  25                  30

<210> SEQ ID NO 20
<211> LENGTH: 20
<212> TYPE: PRT
<213> ORGANISM: Artificial Sequence
<220> FEATURE:
<223> OTHER INFORMATION: Polypeptide

<400> SEQUENCE: 20

Pro Glu Ala His Val Met His Lys Val Ala Pro Arg Pro Gly Gly Gly
1               5                   10                  15

Ser Cys Gly Asp
            20

<210> SEQ ID NO 21
<211> LENGTH: 456
<212> TYPE: DNA
<213> ORGANISM: Artificial Sequence
<220> FEATURE:
<223> OTHER INFORMATION: Synthetic gene

<400> SEQUENCE: 21
ggatccatgg gttccagcgc tgcggcagct gcagcggctg caagtggtcc ggacccggag      60
gcacacgtta tgcacaaagt agcgccgcgt ccgggtggcg gttcttgtgg tgatccgggt     120
agctctgcgg ctgcagctgc ggctgcagct tccggtccgg accggaagc tcacgttatg     180 cacaaggttg ctccacgccc gggcggtggc agctgcggtg atccaggcag ctctgctgcg     240
gctgcggcag cggccgcttc tggccccgac ccggaagctc acgttatgca caaagtggct     300
ccgcgtccgg gtggcggttc ctgcggcgat ccgggttctt ccgctgcagc ggctgcggcc     360
gcagcgtctg gcccggaccc ggaagcacat gttatgcata agtagcgcc gcgtccgggc     420 ggtggctctt gcggtgaccc gggctaatga aagctt                              456

<210> SEQ ID NO 22
<211> LENGTH: 304
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (1)..(15)
<223> OTHER INFORMATION: T7-Tag

<400> SEQUENCE: 22

Met Ala Ser Met Thr Gly Gly Gln Gln Met Gly Arg Gly Ser Met Gly
1               5                   10                  15

Ser Ser Ala Ala Ala Ala Ala Ala Ala Ala Ser Gly Pro Asp Pro Glu

```
                20              25              30
Ala His Val Met His Lys Val Ala Pro Arg Pro Gly Gly Gly Ser Cys
             35              40              45

Gly Asp Pro Gly Ser Ser Ala Ala Ala Ala Ala Ala Ala Ser Gly
 50              55              60

Pro Asp Pro Glu Ala His Val Met His Lys Val Ala Pro Arg Pro Gly
 65              70              75              80

Gly Gly Ser Cys Gly Asp Pro Gly Ser Ser Ala Ala Ala Ala Ala
             85              90              95

Ala Ala Ser Gly Pro Asp Pro Glu Ala His Val Met His Lys Val Ala
            100             105             110

Pro Arg Pro Gly Gly Gly Ser Cys Gly Asp Pro Gly Ser Ser Ala Ala
            115             120             125

Ala Ala Ala Ala Ala Ser Gly Pro Asp Pro Glu Ala His Val Met
            130             135             140

His Lys Val Ala Pro Arg Pro Gly Gly Gly Ser Cys Gly Asp Pro Gly
145             150             155             160

Ser Ser Ala Ala Ala Ala Ala Ala Ala Ser Gly Pro Asp Pro Glu
            165             170             175

Ala His Val Met His Lys Val Ala Pro Arg Pro Gly Gly Gly Ser Cys
            180             185             190

Gly Asp Pro Gly Ser Ser Ala Ala Ala Ala Ala Ala Ala Ser Gly
            195             200             205

Pro Asp Pro Glu Ala His Val Met His Lys Val Ala Pro Arg Pro Gly
            210             215             220

Gly Gly Ser Cys Gly Asp Pro Gly Ser Ser Ala Ala Ala Ala Ala
225             230             235             240

Ala Ala Ser Gly Pro Asp Pro Glu Ala His Val Met His Lys Val Ala
            245             250             255

Pro Arg Pro Gly Gly Gly Ser Cys Gly Asp Pro Gly Ser Ser Ala Ala
            260             265             270

Ala Ala Ala Ala Ala Ser Gly Pro Asp Pro Glu Ala His Val Met
            275             280             285

His Lys Val Ala Pro Arg Pro Gly Gly Gly Ser Cys Gly Asp Pro Gly
            290             295             300

<210> SEQ ID NO 23
<211> LENGTH: 21
<212> TYPE: PRT
<213> ORGANISM: Artificial Sequence
<220> FEATURE:
<223> OTHER INFORMATION: P18 Peptide

<400> SEQUENCE: 23

Pro Gly Lys Trp Lys Leu Phe Lys Lys Ile Pro Lys Phe Leu His Leu
1               5                  10                  15

Ala Lys Lys Phe Gly
            20

<210> SEQ ID NO 24
<211> LENGTH: 450
<212> TYPE: DNA
<213> ORGANISM: Artificial Sequence
<220> FEATURE:
<223> OTHER INFORMATION: Synthetic gene

<400> SEQUENCE: 24
```

```
ggatccatgg gctctagcgc tgcagcggca gctgccgcgg cttctggtcc gggtctgttc    60
gaagagatct ccgaattcct gcagtctctg gaagagttcg gtggcccggg ttcctctgca   120
gctgcggctg cagctgcggc aagcggccct gacccaggta aatggaaact gtttaagaaa   180
attccgaaat tcctgcatct ggctaaaaaa ttcggtgacc cgggttcttc cgctgcggct   240
gcagctgcag ctgcgtccgg tccgggtctg ttcgaagaaa tctccgaatt cctgcagtct   300
ctggaagaat cggcggtcc gggctctagc gctgccgctg cagcggcagc ggcttccggc   360
ccggacccgg gcaaatggaa actgtttaag aaaatcccga aatttctgca tctggctaaa   420
aagttcggcg atccgggcta atgaaagctt                                    450
```

<210> SEQ ID NO 25
<211> LENGTH: 300
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (1)..(15)
<223> OTHER INFORMATION: T7-Tag

<400> SEQUENCE: 25

```
Met Ala Ser Met Thr Gly Gly Gln Gln Met Gly Arg Gly Ser Met Gly
1               5                  10                  15

Ser Ser Ala Ala Ala Ala Ala Ala Ala Ser Gly Pro Gly Leu Phe
            20                  25                  30

Glu Glu Ile Ser Glu Phe Leu Gln Ser Leu Glu Glu Phe Gly Gly Pro
        35                  40                  45

Gly Ser Ser Ala Ala Ala Ala Ala Ala Ala Ser Gly Pro Asp Pro
    50                  55                  60

Gly Lys Trp Lys Leu Phe Lys Lys Ile Pro Lys Phe Leu His Leu Ala
65                  70                  75                  80

Lys Lys Phe Gly Asp Pro Gly Ser Ser Ala Ala Ala Ala Ala Ala
                85                  90                  95

Ala Ser Gly Pro Gly Leu Phe Glu Glu Ile Ser Glu Phe Leu Gln Ser
            100                 105                 110

Leu Glu Glu Phe Gly Gly Pro Gly Ser Ser Ala Ala Ala Ala Ala
        115                 120                 125

Ala Ala Ser Gly Pro Asp Pro Gly Lys Trp Lys Leu Phe Lys Lys Ile
    130                 135                 140

Pro Lys Phe Leu His Leu Ala Lys Lys Phe Gly Asp Pro Gly Ser Ser
145                 150                 155                 160

Ala Ala Ala Ala Ala Ala Ala Ser Gly Pro Gly Leu Phe Glu Glu
                165                 170                 175

Ile Ser Glu Phe Leu Gln Ser Leu Glu Glu Phe Gly Gly Pro Gly Ser
            180                 185                 190

Ser Ala Ala Ala Ala Ala Ala Ala Ser Gly Pro Asp Pro Gly Lys
        195                 200                 205

Trp Lys Leu Phe Lys Lys Ile Pro Lys Phe Leu His Leu Ala Lys Lys
    210                 215                 220

Phe Gly Asp Pro Gly Ser Ser Ala Ala Ala Ala Ala Ala Ala Ser
225                 230                 235                 240

Gly Pro Gly Leu Phe Glu Glu Ile Ser Glu Phe Leu Gln Ser Leu Glu
                245                 250                 255

Glu Phe Gly Gly Pro Gly Ser Ser Ala Ala Ala Ala Ala Ala Ala Ala
```

```
                260                 265                 270
Ser Gly Pro Asp Pro Gly Lys Trp Lys Leu Phe Lys Lys Ile Pro Lys
            275                 280                 285

Phe Leu His Leu Ala Lys Lys Phe Gly Asp Pro Gly
        290                 295                 300

<210> SEQ ID NO 26
<211> LENGTH: 18
<212> TYPE: PRT
<213> ORGANISM: Artificial Sequence
<220> FEATURE:
<223> OTHER INFORMATION: Polypeptide

<400> SEQUENCE: 26

Pro Gly Glu Arg Lys Arg Leu Ile Gly Cys Ser Val Met Thr Lys Pro
1               5                   10                  15

Ala Gly

<210> SEQ ID NO 27
<211> LENGTH: 516
<212> TYPE: DNA
<213> ORGANISM: Artificial Sequence
<220> FEATURE:
<223> OTHER INFORMATION: Synthetic gene

<400> SEQUENCE: 27
ggatccatgg gctcttccgc tgcagccgct gcagctgcgg ctgcatccgg tccggaggca      60
gagccggaag acccgggtga acgtaaacgt ctgatcggtt gttctgtaat gaccaaacct     120
gctggtgatc cgggctccag cgctgcggct gcggcagctg cagcggcctc tggtccggag     180
gcggaaccgg aggacccggg tgaacgtaag cgcctgatcg gctgcagcgt gatgaccaaa     240
ccggctggtg atccgggttc ttccgcggct gcagctgcgg cagctgcagc tagtggtcca     300
gaagcagaac cagaagaccc gggtgaacgt aaacgtctga ttggttgctc tgttatgact     360
aaaccggctg gtgacccggg ctcttccgcg gctgccgcgg ctgcggctgc agctagcggc     420
ccggaagctg aaccggaaga tccgggcgaa cgcaagcgtc tgatcggctg ctccgttatg     480
actaaaccgc tggcgacccc gggctaatga aagctt                              516

<210> SEQ ID NO 28
<211> LENGTH: 344
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (1)..(15)
<223> OTHER INFORMATION: T7-Tag

<400> SEQUENCE: 28

Met Ala Ser Met Thr Gly Gly Gln Gln Met Gly Arg Gly Ser Met Gly
1               5                   10                  15

Ser Ser Ala Ala Ala Ala Ala Ala Ala Ala Ser Gly Pro Glu Ala
            20                  25                  30

Glu Pro Glu Asp Pro Gly Glu Arg Lys Arg Leu Ile Gly Cys Ser Val
        35                  40                  45

Met Thr Lys Pro Ala Gly Asp Pro Gly Ser Ser Ala Ala Ala Ala
    50                  55                  60

Ala Ala Ala Ala Ser Gly Pro Glu Ala Glu Pro Glu Asp Pro Gly Glu
65                  70                  75                  80
```

```
Arg Lys Arg Leu Ile Gly Cys Ser Val Met Thr Lys Pro Ala Gly Asp
            85                  90                  95

Pro Gly Ser Ser Ala Ala Ala Ala Ala Ala Ala Ser Gly Pro
            100                 105                 110

Glu Ala Glu Pro Glu Asp Pro Gly Arg Lys Arg Leu Ile Gly Cys
        115                 120                 125

Ser Val Met Thr Lys Pro Ala Gly Asp Pro Gly Ser Ser Ala Ala
    130                 135                 140

Ala Ala Ala Ala Ala Ala Ser Gly Pro Glu Ala Glu Pro Glu Asp Pro
145                 150                 155                 160

Gly Glu Arg Lys Arg Leu Ile Gly Cys Ser Val Met Thr Lys Pro Ala
                165                 170                 175

Gly Asp Pro Gly Ser Ser Ala Ala Ala Ala Ala Ala Ala Ala Ser
            180                 185                 190

Gly Pro Glu Ala Glu Pro Glu Asp Pro Gly Glu Arg Lys Arg Leu Ile
            195                 200                 205

Gly Cys Ser Val Met Thr Lys Pro Ala Gly Asp Pro Gly Ser Ser Ala
    210                 215                 220

Ala Ala Ala Ala Ala Ala Ala Ser Gly Pro Glu Ala Glu Pro Glu
225                 230                 235                 240

Asp Pro Gly Glu Arg Lys Arg Leu Ile Gly Cys Ser Val Met Thr Lys
                245                 250                 255

Pro Ala Gly Asp Pro Gly Ser Ser Ala Ala Ala Ala Ala Ala Ala
            260                 265                 270

Ala Ser Gly Pro Glu Ala Glu Pro Glu Asp Pro Gly Glu Arg Lys Arg
        275                 280                 285

Leu Ile Gly Cys Ser Val Met Thr Lys Pro Ala Gly Asp Pro Gly Ser
    290                 295                 300

Ser Ala Ala Ala Ala Ala Ala Ala Ala Ser Gly Pro Glu Ala Glu
305                 310                 315                 320

Pro Glu Asp Pro Gly Glu Arg Lys Arg Leu Ile Gly Cys Ser Val Met
                325                 330                 335

Thr Lys Pro Ala Gly Asp Pro Gly
            340

<210> SEQ ID NO 29
<211> LENGTH: 12
<212> TYPE: PRT
<213> ORGANISM: Artificial Sequence
<220> FEATURE:
<223> OTHER INFORMATION: Polypeptide

<400> SEQUENCE: 29

Asn Pro Ser Ser Leu Phe Arg Tyr Leu Pro Ser Asp
1               5                   10

<210> SEQ ID NO 30
<211> LENGTH: 12
<212> TYPE: PRT
<213> ORGANISM: Artificial
<220> FEATURE:
<223> OTHER INFORMATION: Polypeptide

<400> SEQUENCE: 30

His Gly Gly Gly His Gly His Gly Gly His Gly
1               5                   10
```

```
<210> SEQ ID NO 31
<211> LENGTH: 12
<212> TYPE: PRT
<213> ORGANISM: Artificial Sequence
<220> FEATURE:
<223> OTHER INFORMATION: Polypeptide

<400> SEQUENCE: 31

His Tyr Pro Thr Leu Pro Leu Gly Ser Ser Thr Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Polypeptide

<400> SEQUENCE: 32

Ala Leu Ser Pro His Ser Ala Pro Leu Thr Leu Tyr
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Polypeptide

<400> SEQUENCE: 33

Ser Ala Gly Arg Leu Ser Ala
1               5

<210> SEQ ID NO 34
<211> LENGTH: 7
<212> TYPE: PRT
<213> ORGANISM: Artificial Sequence
<220> FEATURE:
<223> OTHER INFORMATION: Polypeptide

<400> SEQUENCE: 34

Thr Leu Pro Asn His Thr Val
1               5

<210> SEQ ID NO 35
<211> LENGTH: 7
<212> TYPE: PRT
<213> ORGANISM: Artificial Sequence
<220> FEATURE:
<223> OTHER INFORMATION: Polypeptide

<400> SEQUENCE: 35

His Thr Ser Lys Leu Gly Ile
1               5

<210> SEQ ID NO 36
<211> LENGTH: 16
<212> TYPE: PRT
<213> ORGANISM: Artificial Sequence
<220> FEATURE:
<223> OTHER INFORMATION: Polypeptide

<400> SEQUENCE: 36

Met Ser Pro His Pro His Pro Arg His His Thr Gly Gly Gly Lys
1               5                   10                  15

<210> SEQ ID NO 37
```

```
<211> LENGTH: 17
<212> TYPE: PRT
<213> ORGANISM: Artificial Sequence
<220> FEATURE:
<223> OTHER INFORMATION: Polypeptide

<400> SEQUENCE: 37

Glu Ala His Val Met His Lys Val Ala Pro Arg Pro Gly Gly Gly Ser
1               5                   10                  15

Cys

<210> SEQ ID NO 38
<211> LENGTH: 18
<212> TYPE: PRT
<213> ORGANISM: Artificial Sequence
<220> FEATURE:
<223> OTHER INFORMATION: Polypeptide

<400> SEQUENCE: 38

Ser Ser Lys Lys Ser Gly Ser Tyr Ser Gly Ser Lys Gly Ser Arg Arg
1               5                   10                  15

Ile Leu

<210> SEQ ID NO 39
<211> LENGTH: 27
<212> TYPE: PRT
<213> ORGANISM: Artificial Sequence
<220> FEATURE:
<223> OTHER INFORMATION: Polypeptide

<400> SEQUENCE: 39

Pro Tyr Ala Tyr Met Lys Ser Arg Asp Ile Glu Ser Ala Gln Ser Asp
1               5                   10                  15

Glu Glu Val Glu Leu Arg Asp Ala Leu Ala Asp
            20                  25

<210> SEQ ID NO 40
<211> LENGTH: 20
<212> TYPE: PRT
<213> ORGANISM: Artificial Sequence
<220> FEATURE:
<223> OTHER INFORMATION: Polypeptide

<400> SEQUENCE: 40

Pro Gly Tyr Gly Tyr Tyr Lys Asn Arg Asn Ala Glu Pro Ala Ala Ala
1               5                   10                  15

Glu Ala Val Asp
            20

<210> SEQ ID NO 41
<211> LENGTH: 20
<212> TYPE: PRT
<213> ORGANISM: Artificial Sequence
<220> FEATURE:
<223> OTHER INFORMATION: Polypeptide

<400> SEQUENCE: 41

Pro Gly Lys Ser Arg Asp Ile Glu Ser Ala Gln Ser Asp Glu Glu Val
1               5                   10                  15

Glu Leu Arg Asp
            20

<210> SEQ ID NO 42
<211> LENGTH: 17
```

```
<212> TYPE: PRT
<213> ORGANISM: Artificial Sequence
<220> FEATURE:
<223> OTHER INFORMATION: Polypeptide

<400> SEQUENCE: 42

Pro Gly Lys Ser Arg Asp Ala Glu Pro Ala Ala Ala Gly Glu Glu Val
1               5                   10                  15
Asp

<210> SEQ ID NO 43
<211> LENGTH: 33
<212> TYPE: PRT
<213> ORGANISM: Artificial Sequence
<220> FEATURE:
<223> OTHER INFORMATION: Polypeptide

<400> SEQUENCE: 43

Ser Ser Lys Lys Ser Gly Ser Tyr Ser Gly Ser Lys Gly Ser Arg Arg
1               5                   10                  15
Ile Leu Gly Gly Gly Asn Pro Ser Ser Leu Phe Arg Tyr Leu Pro Ser
            20                  25                  30
Asp

<210> SEQ ID NO 44
<211> LENGTH: 27
<212> TYPE: PRT
<213> ORGANISM: Artificial Sequence
<220> FEATURE:
<223> OTHER INFORMATION: Polypeptide

<400> SEQUENCE: 44

Met Ser Pro His Pro His Pro Arg His His His Thr Gly Gly Gly Asn
1               5                   10                  15
Pro Ser Ser Leu Phe Arg Tyr Leu Pro Ser Asp
            20                  25

<210> SEQ ID NO 45
<211> LENGTH: 31
<212> TYPE: PRT
<213> ORGANISM: Artificial Sequence
<220> FEATURE:
<223> OTHER INFORMATION: Polypeptide

<400> SEQUENCE: 45

Asn Pro Ser Ser Leu Phe Arg Tyr Leu Pro Ser Asp Gly Gly Gly Arg
1               5                   10                  15
Arg Glu Glu Trp Trp Asp Asp Arg Arg Glu Glu Trp Trp Asp Asp
            20                  25                  30

<210> SEQ ID NO 46
<211> LENGTH: 27
<212> TYPE: PRT
<213> ORGANISM: Artificial Sequence
<220> FEATURE:
<223> OTHER INFORMATION: Polypeptide

<400> SEQUENCE: 46

Met Ser Pro His Pro His Pro Arg His His His Thr Gly Gly Gly His
1               5                   10                  15
Gly Gly Gly His Gly His Gly Gly Gly His Gly
            20                  25
```

```
<210> SEQ ID NO 47
<211> LENGTH: 33
<212> TYPE: PRT
<213> ORGANISM: Artificial Sequence
<220> FEATURE:
<223> OTHER INFORMATION: Polypeptide

<400> SEQUENCE: 47

Ser Ser Lys Lys Ser Gly Ser Tyr Ser Gly Ser Lys Gly Ser Arg Arg
1               5                   10                  15

Ile Leu Gly Gly Gly His Gly Gly Gly His Gly His Gly Gly Gly His
            20                  25                  30

Gly

<210> SEQ ID NO 48
<211> LENGTH: 33
<212> TYPE: PRT
<213> ORGANISM: Artificial Sequence
<220> FEATURE:
<223> OTHER INFORMATION: Polypeptide

<400> SEQUENCE: 48

Ser Ser Lys Lys Ser Gly Ser Tyr Ser Gly Ser Lys Gly Ser Arg Arg
1               5                   10                  15

Ile Leu Gly Gly Gly His Tyr Pro Thr Leu Pro Leu Gly Ser Ser Thr
            20                  25                  30

Tyr

<210> SEQ ID NO 49
<211> LENGTH: 28
<212> TYPE: PRT
<213> ORGANISM: Artificial Sequence
<220> FEATURE:
<223> OTHER INFORMATION: Polypeptide

<400> SEQUENCE: 49

Ser Ser Lys Lys Ser Gly Ser Tyr Ser Gly Ser Lys Gly Ser Arg Arg
1               5                   10                  15

Ile Leu Gly Gly Gly Ser Ala Gly Arg Leu Ser Ala
            20                  25

<210> SEQ ID NO 50
<211> LENGTH: 16
<212> TYPE: PRT
<213> ORGANISM: Artificial Sequence
<220> FEATURE:
<223> OTHER INFORMATION: Polypeptide

<400> SEQUENCE: 50

Arg Arg Glu Glu Trp Trp Asp Asp Arg Arg Glu Glu Trp Trp Asp Asp
1               5                   10                  15

<210> SEQ ID NO 51
<211> LENGTH: 21
<212> TYPE: PRT
<213> ORGANISM: Artificial Sequence
<220> FEATURE:
<223> OTHER INFORMATION: Polypeptide

<400> SEQUENCE: 51

Met Lys Gln Leu Ala Asp Ser Leu Met Gln Leu Ala Arg Gln Val Ser
1               5                   10                  15

Arg Leu Glu Ser Ala
            20
```

```
<210> SEQ ID NO 52
<211> LENGTH: 21
<212> TYPE: PRT
<213> ORGANISM: Artificial Sequence
<220> FEATURE:
<223> OTHER INFORMATION: Polypeptide

<400> SEQUENCE: 52

Met Lys Gln Leu Ala Asp Ser Leu His Gln Leu Ala Arg Gln Val Ser
1               5                   10                  15

Arg Leu Glu His Ala
            20

<210> SEQ ID NO 53
<211> LENGTH: 28
<212> TYPE: PRT
<213> ORGANISM: Artificial Sequence
<220> FEATURE:
<223> OTHER INFORMATION: Polypeptide

<400> SEQUENCE: 53

Leu Met Gln Leu Ala Arg Gln Met Lys Gln Leu Ala Asp Ser Leu Met
1               5                   10                  15

Gln Leu Ala Arg Gln Val Ser Arg Leu Glu Ser Ala
            20                  25

<210> SEQ ID NO 54
<211> LENGTH: 21
<212> TYPE: PRT
<213> ORGANISM: Artificial Sequence
<220> FEATURE:
<223> OTHER INFORMATION: Polypeptide

<400> SEQUENCE: 54

Met Lys Glu Leu Ala Asp Ser Leu Met Gln Leu Ala Arg Gln Val Asp
1               5                   10                  15

Arg Leu Glu Ser Ala
            20

<210> SEQ ID NO 55
<211> LENGTH: 21
<212> TYPE: PRT
<213> ORGANISM: Artificial Sequence
<220> FEATURE:
<223> OTHER INFORMATION: Polypeptide

<400> SEQUENCE: 55

Met Lys Gln Leu Ala Asp Ser Leu His Gln Leu Ala His Gln Val Ser
1               5                   10                  15

His Leu Glu His Ala
            20

<210> SEQ ID NO 56
<211> LENGTH: 9
<212> TYPE: PRT
<213> ORGANISM: Artificial Sequence
<220> FEATURE:
<223> OTHER INFORMATION: Polypeptide

<400> SEQUENCE: 56

Pro His Phe Arg Phe Ser Phe Ser Pro
1               5
```

```
<210> SEQ ID NO 57
<211> LENGTH: 9
<212> TYPE: PRT
<213> ORGANISM: Artificial Sequence
<220> FEATURE:
<223> OTHER INFORMATION: Polypeptide

<400> SEQUENCE: 57

Pro His Phe Ser Phe Ser Phe Ser Pro
1               5

<210> SEQ ID NO 58
<211> LENGTH: 9
<212> TYPE: PRT
<213> ORGANISM: Artificial Sequence
<220> FEATURE:
<223> OTHER INFORMATION: Polypeptide

<400> SEQUENCE: 58

Pro Ser Phe Arg Phe Ser Phe Ser Pro
1               5

<210> SEQ ID NO 59
<211> LENGTH: 21
<212> TYPE: PRT
<213> ORGANISM: Artificial Sequence
<220> FEATURE:
<223> OTHER INFORMATION: Polypeptide

<400> SEQUENCE: 59

Met Glu Glu Leu Ala Asp Ser Leu Glu Glu Leu Ala Arg Gln Val Glu
1               5                   10                  15

Glu Leu Glu Ser Ala
            20

<210> SEQ ID NO 60
<211> LENGTH: 21
<212> TYPE: PRT
<213> ORGANISM: Artificial Sequence
<220> FEATURE:
<223> OTHER INFORMATION: Polypeptide

<400> SEQUENCE: 60

Met Lys Lys Leu Ala Asp Ser Leu Lys Lys Leu Ala Arg Gln Val Lys
1               5                   10                  15

Lys Leu Glu Ser Ala
            20

<210> SEQ ID NO 61
<211> LENGTH: 9
<212> TYPE: PRT
<213> ORGANISM: Artificial Sequence
<220> FEATURE:
<223> OTHER INFORMATION: Polypeptide

<400> SEQUENCE: 61

Pro His Phe His Phe Ser Phe Ser Pro
1               5

<210> SEQ ID NO 62
<211> LENGTH: 9
<212> TYPE: PRT
<213> ORGANISM: Artificial Sequence
<220> FEATURE:
<223> OTHER INFORMATION: Polypeptide

<400> SEQUENCE: 62
```

```
Pro His Phe Ser Phe His Phe Ser Pro
1               5
```

<210> SEQ ID NO 63
<211> LENGTH: 21
<212> TYPE: PRT
<213> ORGANISM: Artificial Sequence
<220> FEATURE:
<223> OTHER INFORMATION: Polypeptide

<400> SEQUENCE: 63

```
Met Lys Gln Leu Ala Asp Ser Leu His Gln Leu Ala His Lys Val Ser
1               5                   10                  15

His Leu Glu His Ala
            20
```

<210> SEQ ID NO 64
<211> LENGTH: 21
<212> TYPE: PRT
<213> ORGANISM: Artificial Sequence
<220> FEATURE:
<223> OTHER INFORMATION: Polypeptide

<400> SEQUENCE: 64

```
Glu Ile Ser Ala Leu Glu Lys Glu Ile Ser Ala Leu Glu Lys Glu Ile
1               5                   10                  15

Ser Ala Leu Glu Lys
            20
```

<210> SEQ ID NO 65
<211> LENGTH: 21
<212> TYPE: PRT
<213> ORGANISM: Artificial Sequence
<220> FEATURE:
<223> OTHER INFORMATION: Polypeptide

<400> SEQUENCE: 65

```
Lys Ile Ser Ala Leu Lys Glu Lys Ile Ser Ala Leu Lys Glu Lys Ile
1               5                   10                  15

Ser Ala Leu Lys Glu
            20
```

<210> SEQ ID NO 66
<211> LENGTH: 16
<212> TYPE: PRT
<213> ORGANISM: Artificial Sequence
<220> FEATURE:
<223> OTHER INFORMATION: Polypeptide

<400> SEQUENCE: 66

```
Arg Ala Asp Ala Arg Ala Asp Ala Arg Ala Asp Ala Arg Ala Asp Ala
1               5                   10                  15
```

<210> SEQ ID NO 67
<211> LENGTH: 21
<212> TYPE: PRT
<213> ORGANISM: Artificial Sequence
<220> FEATURE:
<223> OTHER INFORMATION: Polypeptide

<400> SEQUENCE: 67

```
Val Lys Val Lys Val Lys Val Lys Val Gly Pro Pro Thr Lys Val Lys
1               5                   10                  15

Val Lys Val Lys Val
```

20

<210> SEQ ID NO 68
<211> LENGTH: 6
<212> TYPE: PRT
<213> ORGANISM: Artificial Sequence
<220> FEATURE:
<223> OTHER INFORMATION: Peptide

<400> SEQUENCE: 68

Glu Ala Glu Pro Glu Asp
1               5

<210> SEQ ID NO 69
<211> LENGTH: 22
<212> TYPE: PRT
<213> ORGANISM: Artificial Sequence
<220> FEATURE:
<223> OTHER INFORMATION: Peptide

<400> SEQUENCE: 69

Pro Gly Lys Trp Lys Leu Phe Lys Lys Ile Pro Lys Phe Leu His Leu
1               5                   10                  15

Ala Lys Lys Phe Gly Asp
            20

<210> SEQ ID NO 70
<211> LENGTH: 19
<212> TYPE: PRT
<213> ORGANISM: Artificial Sequence
<220> FEATURE:
<223> OTHER INFORMATION: Peptide

<400> SEQUENCE: 70

Pro Gly Glu Arg Lys Arg Leu Ile Gly Cys Ser Val Met Thr Lys Pro
1               5                   10                  15

Ala Gly Asp

<210> SEQ ID NO 71
<211> LENGTH: 22
<212> TYPE: PRT
<213> ORGANISM: Artificial Sequence
<220> FEATURE:
<223> OTHER INFORMATION: Peptide

<400> SEQUENCE: 71

Pro Gly Lys Trp Lys Leu Phe Lys Lys Ile Pro Lys Phe Leu His Leu
1               5                   10                  15

Ala Lys Lys Phe Gly Asn
            20

<210> SEQ ID NO 72
<211> LENGTH: 15
<212> TYPE: PRT
<213> ORGANISM: Artificial Sequence
<220> FEATURE:
<223> OTHER INFORMATION: Peptide

<400> SEQUENCE: 72

Glu Arg Lys Arg Leu Ile Gly Cys Ser Val Met Thr Lys Pro Ala
1               5                   10                  15

<210> SEQ ID NO 73
<211> LENGTH: 12
<212> TYPE: PRT

<210> SEQ ID NO 74
<211> LENGTH: 456
<212> TYPE: DNA
<213> ORGANISM: Artificial Sequence
<220> FEATURE:
<223> OTHER INFORMATION: Synthetic gene

<400> SEQUENCE: 74

```
ggatccatgg cgctgcagc ggcagctgcc gcggcttctg gtccgggtga gtgggagctg      60
ttcgaagaga tcagcgaatt cctgcagtct ctggaagagt tcggtggccc gggttcctct    120
gctgctgcgg ctgcagctgc ggcaggcccg ggcgacccag gtaaatggaa actgtttaag    180
aaaattccga aattcctgca tctggctaaa aaattcggtg acccgggttc ctctgctgcg    240
gctgcagctg cagctgcgtc cggtccgggt gaatgggaac tgttcgaaga aatctccgaa    300
ttcctgcagt ctctggaaga attcggcggt ccgggcgctg ccgctgcagc ggcagcggct    360
ggtcctggcg acccgggcaa atggaaactg tttaagaaaa tcccgaaatt tctgcatctg    420
gctaaaaagt tcggcgatcc gggctaatga aagctt                               456
```

<210> SEQ ID NO 75
<211> LENGTH: 304
<212> TYPE: PRT
<213> ORGANISM: Artificial Sequence
<220> FEATURE:
<223> OTHER INFORMATION: Polypeptide

<400> SEQUENCE: 75

Met Ala Ser Met Thr Gly Gly Gln Gln Met Gly Arg Gly Ser Met Gly
1               5                   10                  15
Ala Ala Ala Ala Ala Ala Ala Ala Ser Gly Pro Gly Glu Trp Glu Leu
            20                  25                  30
Phe Glu Glu Ile Ser Glu Phe Leu Gln Ser Leu Glu Glu Phe Gly Gly
        35                  40                  45
Pro Gly Ser Ser Ala Ala Ala Ala Ala Ala Ala Gly Pro Gly Asp
    50                  55                  60
Pro Gly Lys Trp Lys Leu Phe Lys Lys Ile Pro Lys Phe Leu His Leu
65                  70                  75                  80
Ala Lys Lys Phe Gly Asp Pro Gly Ser Ser Ala Ala Ala Ala Ala
            85                  90                  95
Ala Ala Ser Gly Pro Gly Glu Trp Glu Leu Phe Glu Glu Ile Ser Glu
            100                 105                 110
Phe Leu Gln Ser Leu Glu Glu Phe Gly Gly Pro Gly Ala Ala Ala Ala
        115                 120                 125
Ala Ala Ala Ala Gly Pro Gly Asp Pro Gly Lys Trp Lys Leu Phe Lys
    130                 135                 140
Lys Ile Pro Lys Phe Leu His Leu Ala Lys Lys Phe Gly Asp Pro Gly
145                 150                 155                 160
Ala Ala Ala Ala Ala Ala Ala Ala Ser Gly Pro Gly Glu Trp Glu Leu
            165                 170                 175
Phe Glu Glu Ile Ser Glu Phe Leu Gln Ser Leu Glu Glu Phe Gly Gly

```
            180                 185                 190
Pro Gly Ser Ser Ala Ala Ala Ala Ala Gly Pro Gly Asp
            195                 200                 205

Pro Gly Lys Trp Lys Leu Phe Lys Lys Ile Pro Lys Phe Leu His Leu
            210                 215                 220

Ala Lys Lys Phe Gly Asp Pro Gly Ser Ser Ala Ala Ala Ala Ala
225                 230                 235                 240

Ala Ala Ser Gly Pro Gly Glu Trp Glu Leu Phe Glu Glu Ile Ser Glu
                245                 250                 255

Phe Leu Gln Ser Leu Glu Glu Phe Gly Gly Pro Gly Ala Ala Ala Ala
                260                 265                 270

Ala Ala Ala Gly Pro Gly Asp Pro Gly Lys Trp Lys Leu Phe Lys
            275                 280                 285

Lys Ile Pro Lys Phe Leu His Leu Ala Lys Lys Phe Gly Asp Pro Gly
            290                 295                 300
```

<210> SEQ ID NO 76
<211> LENGTH: 438
<212> TYPE: DNA
<213> ORGANISM: Artificial Sequence
<220> FEATURE:
<223> OTHER INFORMATION: Synthetic gene

<400> SEQUENCE: 76

```
ggatccatgg gcgctgcagc ggcagctgcc gcggcttctg gtccgggtga gtgggagctg     60
ttcgaagaga tcagcgaatt cctgcagtct ctggaagagt tcggtggccc gggttcctct    120
gctgctgcgg ctgcagctgc ggcaggccca ggcgacaaat ggaaactgtt taagaaaatt    180
ccgaaattcc tgcatctggc taaaaaattc gacccgggtt cctctgctgc ggctgcagct    240
gcagctgcgt ccggtccggg tgaatgggaa ctgttcgaag aaatctccga attcctgcag    300
tctctggaag aattcggcgg tccgggcgct gccgctgcag cggcagcggc tggtcctggc    360
gacaaatgga aactgtttaa gaaaatcccg aaatttctgc atctggctaa aaagttcgat    420
ccgggctaat gaaagctt                                                  438
```

<210> SEQ ID NO 77
<211> LENGTH: 278
<212> TYPE: PRT
<213> ORGANISM: Artificial Sequence
<220> FEATURE:
<223> OTHER INFORMATION: Polypeptide

<400> SEQUENCE: 77

```
Met Gly Ala Ala Ala Ala Ala Ala Ala Ser Gly Pro Gly Glu Trp
1               5                   10                  15

Glu Leu Phe Glu Glu Ile Ser Glu Phe Leu Gln Ser Leu Glu Glu Phe
                20                  25                  30

Gly Gly Pro Gly Ser Ser Ala Ala Ala Ala Ala Ala Ala Gly Pro
            35                  40                  45

Gly Asp Lys Trp Lys Leu Phe Lys Lys Ile Pro Lys Phe Leu His Leu
50                  55                  60

Ala Lys Lys Phe Asp Pro Gly Ser Ser Ala Ala Ala Ala Ala Ala
65                  70                  75                  80

Ala Ser Gly Pro Gly Glu Trp Glu Leu Phe Glu Glu Ile Ser Glu Phe
                85                  90                  95

Leu Gln Ser Leu Glu Glu Phe Gly Gly Pro Gly Ala Ala Ala Ala Ala
                100                 105                 110
```

-continued

```
Ala Ala Ala Gly Pro Gly Asp Lys Trp Lys Leu Phe Lys Lys Ile Pro
        115             120                 125
Lys Phe Leu His Leu Ala Lys Lys Phe Asp Pro Gly Ala Ala Ala Ala
        130             135                 140
Ala Ala Ala Ala Ser Gly Pro Gly Glu Trp Glu Leu Phe Glu Glu Ile
145                 150             155                     160
Ser Glu Phe Leu Gln Ser Leu Glu Glu Phe Gly Gly Pro Gly Ser Ser
                165             170                     175
Ala Ala Ala Ala Ala Ala Ala Gly Pro Gly Asp Lys Trp Lys Leu
                180             185             190
Phe Lys Lys Ile Pro Lys Phe Leu His Leu Ala Lys Lys Phe Asp Pro
        195             200             205
Gly Ser Ser Ala Ala Ala Ala Ala Ala Ala Ser Gly Pro Gly Glu
    210             215             220
Trp Glu Leu Phe Glu Glu Ile Ser Glu Phe Leu Gln Ser Leu Glu Glu
225                 230             235             240
Phe Gly Gly Pro Gly Ala Ala Ala Ala Ala Ala Ala Gly Pro Gly
                245             250             255
Asp Lys Trp Lys Leu Phe Lys Lys Ile Pro Lys Phe Leu His Leu Ala
        260             265             270
Lys Lys Phe Asp Pro Gly
        275
```